(12) United States Patent
Seeman et al.

(10) Patent No.: US 7,598,363 B2
(45) Date of Patent: Oct. 6, 2009

(54) POLYGONAL NANOSTRUCTURES OF POLYNUCLEIC ACID MULTI-CROSSOVER MOLECULES AND ASSEMBLY OF LATTICES BASED ON DOUBLE CROSSOVER COHESION

(75) Inventors: Nadrian C. Seeman, New York, NY (US); Baoquan Ding, New York, NY (US); Pamela E. Constantinou, New York, NY (US); Tong Wang, Brooklyn, NY (US); Jens Kopatsch, Brooklyn, NY (US); Xiaoping Zhang, Woodside, NY (US); Ruojie Sha, Pomona, NY (US); Lisa Israel, New York, NY (US)

(73) Assignee: New York University, New York, NY (US)

( * ) Notice: Subject to any disclaimer, the term of this patent is extended or adjusted under 35 U.S.C. 154(b) by 328 days.

(21) Appl. No.: 11/148,423

(22) Filed: Jun. 9, 2005

(65) Prior Publication Data
US 2006/0078910 A1  Apr. 13, 2006

Related U.S. Application Data

(60) Provisional application No. 60/578,306, filed on Jun. 10, 2004.

(51) Int. Cl.
*C07H 21/00* (2006.01)
(52) U.S. Cl. ..................... 536/23.1; 536/25.3
(58) Field of Classification Search ...................... None
See application file for complete search history.

(56) References Cited

U.S. PATENT DOCUMENTS 6,072,044 A * 6/2000 Seeman et al. ............. 536/22.1
6,255,469 B1 * 7/2001 Seeman et al. ............. 536/23.1

OTHER PUBLICATIONS

Seeman et al (Nature (Jan. 2003) 421:427-431).*
LaBean et al (J. Am. Chem. Soc. (2000) 122:1848-1860).*

* cited by examiner

*Primary Examiner*—Gary Benzion
*Assistant Examiner*—Stephanie K Mummert
(74) *Attorney, Agent, or Firm*—Browdy and Neimark, PLLC

(57) ABSTRACT

Robust nucleic acid arrays and lattices are assembled based on double crossover cohesion of polygonal units whose edges are composed of nucleic acid multi-crossover domains.

18 Claims, 14 Drawing Sheets

(a)
(b)
Fig. 1A 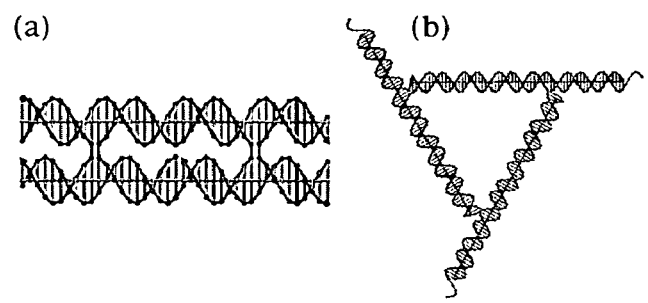 Fig. 1B
(c) (d)
Fig. 1C 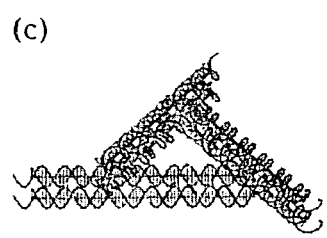 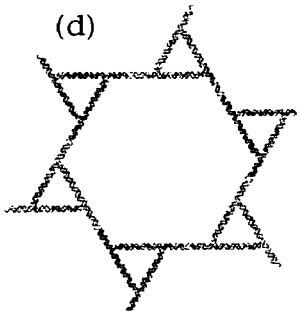 Fig. 1D
(e)

Fig. 2B

SEQUENCE LISTING

```
<160> NUMBER OF SEQ ID NOS: 152

<210> SEQ ID NO 1
<211> LENGTH: 126
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 1 of DX Triangle

<400> SEQUENCE: 1
gaggcaacga actcggctag aacagactgg tcgcaatgtc ctgctgagct gcctgacctt      60
agaattggcg tcttgataat atccgtactc ctcgtcaatc catgaatact tcatctgagt     120
ttgttc                                                                126
```

```
<210> SEQ ID NO 2
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2 of DX Triangle

<400> SEQUENCE: 2
agatgtacca gaactaactc                                               20

<210> SEQ ID NO 3
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3 of DX Triangle

<400> SEQUENCE: 3
gtcctagagt cacgctacgt cactcc                                        26

<210> SEQ ID NO 4
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4 of DX Triangle

<400> SEQUENCE: 4
aagacaccgt ggactttatc                                               20

<210> SEQ ID NO 5
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5 of DX Triangle

<400> SEQUENCE: 5
ctacacgaga tatagaaaca cacatc                                        26

<210> SEQ ID NO 6
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6 of DX Triangle

<400> SEQUENCE: 6
gaccacaacg ggcatattgc                                               20

<210> SEQ ID NO 7
<211> LENGTH: 26
<212> TYPE: DNA
```

```
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7 of DX Triangle

<400> SEQUENCE: 7
ctcaccgaat caatagtcat cgtctc                                             26

<210> SEQ ID NO 8
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8A of DX Triangle

<400> SEQUENCE: 8
ctatgagaga cgatgatcta cgagtatagt tgttgcctcg aacatatacg aataggtgcg        60
cggcggtcgt aaggctgtct gttc                                               84

<210> SEQ ID NO 9
<211> LENGTH: 104
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8B of DX Triangle

<400> SEQUENCE: 9
tagccgagtt cctatactcg tagaaggatg agtggcatta cctattcgta taagttctgg        60
tatcgcgttc cgaagatagt gtgcaaatcg ttacagcgtg actc                        104

<210> SEQ ID NO 10
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9A of DX Triangle

<400> SEQUENCE: 10
tagaccggag tgacgtgcat cagttgctct taggagtacg gataactgtg agcgcctcac        60
tatcttcgga acgcgaaagt attc                                               84

<210> SEQ ID NO 11
<211> LENGTH: 104
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9B of DX Triangle

<400> SEQUENCE: 11
atggattgac ggagcaactg atgcgtaacg atttgcatta ggcgctcaca gtagtccacg        60
gttggtgttc agtgtatggc cgtgctatcg agcatctata tctc                        104
```

```
<210> SEQ ID NO 12
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10A of DX Triangle

<400> SEQUENCE: 12
cacctggatg tgtgttgaag cgaaccatct tagctcagca ggacgacatg gtagtggggc      60
catacactga acaccagcca attc                                            84

<210> SEQ ID NO 13
<211> LENGTH: 104
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10B of DX Triangle

<400> SEQUENCE: 13
taaggtcagg cgatggttcg cttctgctcg atagcacttc cactaccatg tcatgcccgt     60
tgagccttac gaccgccgcg ctgccactca tcctctattg attc                      104

<210> SEQ ID NO 14
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3-2 of DX Triangle

<400> SEQUENCE: 14
taggacgagt cacgctacgt cactcc                                          26

<210> SEQ ID NO 15
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5-2 of DX Triangle

<400> SEQUENCE: 15
gtgtaggaga tatagaaaca cacatc                                          26

<210> SEQ ID NO 16
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7-2 of DX Triangle

<400> SEQUENCE: 16
ggtgaggaat caatagtcat cgtctc                                          26
```

<210> SEQ ID NO 17
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8A-2 of DX Triangle

<400> SEQUENCE: 17
tcataggaga cgatgatcta cgagtatagt tgttgcctcg aacatatacg aataggtgcg    60
cggcggtcgt aaggctgtct gttc                                          84

<210> SEQ ID NO 18
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9A-2 of DX Triangle

<400> SEQUENCE: 18
ggtctaggag tgacgtgcat cagttgctct taggagtacg gataactgtg agcgcctcac    60
tatcttcgga acgcgaaagt attc                                          84

<210> SEQ ID NO 19
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10A-2 of DX Triangle

<400> SEQUENCE: 19
caggtggatg tgtgttgaag cgaaccatct tagctcagca ggacgacatg gtagtggggc    60
catacactga acaccagcca attc                                          84

<210> SEQ ID NO 20
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 1 of Six-Helix Bundle Array

<400> SEQUENCE: 20
gttgcttgat ggagcagacc tatcgtca                                      28

<210> SEQ ID NO 21
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2 of Six-Helix Bundle Array

<400> SEQUENCE: 21
ctgacgtgac gataggacac atcagatgtc ttaggagagg tcacagtaac cttcgacaat    60
cgc                                                                  63

<210> SEQ ID NO 22
<211> LENGTH: 133
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3 of Six-Helix Bundle Array

<400> SEQUENCE: 22
gaagcgtgtc tagcgtcgtg cgactggcat gtgatacata cactggttgg actacatcgc    60
attcactcct aactacgaca tagcctggct catgcaatac ggtcgttgcg ttatggtact   120
agcagtcaac tgc                                                     133

<210> SEQ ID NO 23
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4 of Six-Helix Bundle Array

<400> SEQUENCE: 23
agtgcggatt gatcggatgc cagacgcatc gtggccgatg agcctactcg accaactcaa    60
cgc                                                                  63

<210> SEQ ID NO 24
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5 of Six-Helix Bundle Array

<400> SEQUENCE: 24
tcatggctgt ccgtgcaacc gatcaatc                                       28

<210> SEQ ID NO 25
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6 of Six-Helix Bundle Array

<400> SEQUENCE: 25
tacgccaacg gtacagtggt gactccaacc ttgtaacgtc ctcgataacg ctggacattg    60
cca                                                                  63

<210> SEQ ID NO 26
<211> LENGTH: 65
<212> TYPE: DNA
<213> ORGANISM: Artificial
<220> FEATURE:
<223> OTHER INFORMATION: Synthetic

```
<220> FEATURE:
<221> NAME/KEY: misc_feature
<223> OTHER INFORMATION: Strand 7 of Six-Helix Bundle Array

<400> SEQUENCE: 26
cgcttcgcag ttgactgcta gtacctgagc actgaatgcg atgtagaagt agctctgctc      60
catca                                                                 65

<210> SEQ ID NO 27
<211> LENGTH: 133
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8 of Six-Helix Bundle Array

<400> SEQUENCE: 27
cgtcaggcgt tgagttggtc gagtacgctc ttggttactg tgacctgtgc tcacgaggac      60
gttacaacac ctcacggcca cgatgcgtga actatgacat ctgatgtgtg ctacttgtca     120
ccactgtacc gtt                                                       133

<210> SEQ ID NO 28
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9 of Six-Helix Bundle Array

<400> SEQUENCE: 28
agcaacgatc caatggaacg accgtattgc tgaggtgagt gtatgtatca cttgcacgga      60
cag                                                                   63

<210> SEQ ID NO 29
<211> LENGTH: 61
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10 of Six-Helix Bundle Array

<400> SEQUENCE: 29
ccatgaggca gatacgaaga gcgaggctat gtcgtagata gttctcgcac gacgctagac      60
a                                                                     61

<210> SEQ ID NO 30
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 11 of Six-Helix Bundle Array

<400> SEQUENCE: 30
ggcgtagcga ttgtcgaacg tatctgcc                                        28
```

```
<210> SEQ ID NO 31
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 12 of Six-Helix Bundle Array

<400> SEQUENCE: 31
cgcacttggc aatgtccacc attggatc                                      28

<210> SEQ ID NO 32
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-1-22 of Triangle Motif (skewed
      TX triangle)

<400> SEQUENCE: 32
ctcgaagtgg cgtatctcgt tg                                            22

<210> SEQ ID NO 33
<211> LENGTH: 41
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-2A-41 of Triangle Motif (skewed
      TX triangle)

<400> SEQUENCE: 33
gcactggatc taacgacagc ctcgatggac gcctgcatac c                       41

<210> SEQ ID NO 34
<211> LENGTH: 73
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-2B-73 of Triangle Motif (skewed
      TX triangle)

<400> SEQUENCE: 34
gagcttcaca gtatcctcta gttgacatcc gagtgccata gacctgacct ggaacactta   60
cgcgatctta gct                                                      73

<210> SEQ ID NO 35
<211> LENGTH: 43
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-2C-43 of Triangle Motif (skewed
      TX triangle)

<400> SEQUENCE: 35
gtacttggat tgctccagac gtagacttga cttcgagcac agc                     43
```

<210> SEQ ID NO 36
<211> LENGTH: 48
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-3A-48 of Triangle Motif (skewed
      TX triangle)

<400> SEQUENCE: 36
gagctgccta gtattgttgc atcatgccgt ggagtgtagc tctcgacg                48

<210> SEQ ID NO 37
<211> LENGTH: 46
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-3B-46 of Triangle Motif (skewed
      TX triangle)

<400> SEQUENCE: 37
cttagagcga tatactcacg ttgctgtcgt tagatggaga ctagcc                  46

<210> SEQ ID NO 38
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-3C-50 of Triangle Motif (skewed
      TX triangle)

<400> SEQUENCE: 38
gctggtagca ccatcgagcg tgagtggtct atgcgtacac acaagtctac              50

<210> SEQ ID NO 39
<211> LENGTH: 77
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-3D-77 of Triangle Motif (skewed
      TX triangle)

<400> SEQUENCE: 39
gtctggagca atggtcaata tcgctctaag cgtcgagagc tactaatcta tccggtgtat   60
gtcctgcgga ccaacga                                                  77

<210> SEQ ID NO 40
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-4-20 of Triangle Motif (skewed
      TX triangle)

```
<400> SEQUENCE: 40
gtccgcacct actcgctgtg                                                    20

<210> SEQ ID NO 41
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-5-22 of Triangle Motif (skewed
      TX triangle)

<400> SEQUENCE: 41
gagattgtgg cagctccgct ac                                                 22

<210> SEQ ID NO 42
<211> LENGTH: 41
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-6A-41 of Triangle Motif (skewed
      TX triangle)

<400> SEQUENCE: 42
gagtaggaat agttctcaac catgtaggac tcctcgcgta a                            41

<210> SEQ ID NO 43
<211> LENGTH: 73
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-6B-73 of Triangle Motif (skewed
      TX triangle)

<400> SEQUENCE: 43
gtgttccacc aagtacagct aagaacggca tgatgccagc atcctgtcct gactgtagag        60
taacacatat tct                                                           73

<210> SEQ ID NO 44
<211> LENGTH: 43
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-6C-43 of Triangle Motif (skewed
      TX triangle)

<400> SEQUENCE: 44
gtatagtgac gcggcaagcg acggtgcaga caatctccgt cag                          43

<210> SEQ ID NO 45
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
```

-continued

<223> OTHER INFORMATION: Strand 3DDXTXT-7A-51 of Triangle Motif (skewed
     TX triangle)

<400> SEQUENCE: 45
ggatcacctg taaccgttgc tatcggtcgt ggcgtgaatg cctgagtctt g    51

<210> SEQ ID NO 46
<211> LENGTH: 43
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-7B-43 of Triangle Motif (skewed
     TX triangle)

<400> SEQUENCE: 46
cgaatcaatg actaccgttg ttgagaacta ttggacatac acc    43

<210> SEQ ID NO 47
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-7C-51 of Triangle Motif (skewed
     TX triangle)

<400> SEQUENCE: 47
ggatagatta cctacatgcg gtagtggatg ctgcaatact actgcaccgt c    51

<210> SEQ ID NO 48
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-7D-76 of Triangle Motif (skewed
     TX triangle)

<400> SEQUENCE: 48
gcttgccgcg tggacacatt gattcgcaag actcaggcat tcttcgcgct agacggctca    60
agctgagacc gtagcg    76

<210> SEQ ID NO 49
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-8-20 of Triangle Motif (skewed
     TX triangle)

<400> SEQUENCE: 49
ggtctcaccg aacgctgacg    20

<210> SEQ ID NO 50
<211> LENGTH: 22
<212> TYPE: DNA
<213> ORGANISM: Artificial
<220> FEATURE:

```
<223> OTHER INFORMATION: Synthetic
<220> FEATURE:
<221> NAME/KEY: misc_feature
<223> OTHER INFORMATION: Strand 3DDXTXT-9-22 of Triangle Motif (skewed
      TX triangle)

<400> SEQUENCE: 50
cgacgtgtgg tgatccgcca tc                                          22

<210> SEQ ID NO 51
<211> LENGTH: 41
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-10A-41 of Triangle Motif (skewed
      TX triangle)

<400> SEQUENCE: 51
cgttcggagt tacgaagcgc cagtacggac gcctgttact c                     41

<210> SEQ ID NO 52
<211> LENGTH: 73
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-10B-73 of Triangle Motif (skewed
      TX triangle)

<400> SEQUENCE: 52
tacagtcaca ctatacagaa tatgacgacc gatagccaat catctgacct gaagctcggt  60
atgcacaact aga                                                    73

<210> SEQ ID NO 53
<211> LENGTH: 59
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-10C-43 of Triangle Motif (skewed
      TX triangle)

<400> SEQUENCE: 53
ggtatgcaca actagaggat actgaccgct catacgatga gttcgacacg tcggcagtc   59

<210> SEQ ID NO 54
<211> LENGTH: 48
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-11A-48 of Triangle Motif (skewed
      TX triangle)

<400> SEQUENCE: 54
gatacgcctg tgtacgttgc actcggatgt ggcgtggtac gacgagtc               48

<210> SEQ ID NO 55
<211> LENGTH: 44
```

```
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-11B-44 of Triangle Motif (skewed
      TX triangle)

<400> SEQUENCE: 55
gatcagtctg aggacgcacg ttgcgcttcg taactgcttg agcc                44

<210> SEQ ID NO 56
<211> LENGTH: 53
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-11C-53 of Triangle Motif (skewed
      TX triangle)

<400> SEQUENCE: 56
gtctagcgcg aaccgtactg cgtgcgtgat gattgcggtt acacgaactc atc       53

<210> SEQ ID NO 57
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-11D-76 of Triangle Motif (skewed
      TX triangle)

<400> SEQUENCE: 57
gtatgagcgg tggtcacctc agactgatcg actcgtcgta cctgctacca gcggctagtc  60
tcctgtcatg gatggc                                                 76

<210> SEQ ID NO 58
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-12-20 of Triangle Motif (skewed
      TX triangle)

<400> SEQUENCE: 58
catgacacca gtgcgactgc                                             20

<210> SEQ ID NO 59
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-1BE-22 of Triangle Motif (skewed
      TX triangle)

<400> SEQUENCE: 59
gctgtgctcg aagtggcgta tc                                          22
```

<210> SEQ ID NO 60
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-4BE-20 of Triangle Motif (skewed TX triangle)

<400> SEQUENCE: 60
tcgttggtcc gcacctactc         20

<210> SEQ ID NO 61
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-5BE-22 of Triangle Motif (skewed TX triangle)

<400> SEQUENCE: 61
ctgacggaga ttgtggcagc tc         22

<210> SEQ ID NO 62
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-8BE-20 of Triangle Motif (skewed TX triangle)

<400> SEQUENCE: 62
cgctacggtc tcaccgaacg         20

<210> SEQ ID NO 63
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-9BE-22 of Triangle Motif (skewed TX triangle)

<400> SEQUENCE: 63
gactgccgac gtgtggtgat cc         22

<210> SEQ ID NO 64
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3DDXTXT-12BE-20 of Triangle Motif (skewed TX triangle)

<400> SEQUENCE: 64
gccatccatg acaccagtgc         20

<210> SEQ ID NO 65
<211> LENGTH: 126
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 1 of DX-Parallelogram (PDX-E-E)

<400> SEQUENCE: 65
ctcataagta atgatacttc gtaatctagc ttgcaggcgt gaatacatct tcgcagacac    60
cgccatgtaa ctgctgaacg ccgatgatgt tctctgaagt tccttgcaca acagttcact   120
gcgtca                                                              126

<210> SEQ ID NO 66
<211> LENGTH: 126
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2 of DX-Parallelogram (PDX-E-E)

<400> SEQUENCE: 66
cttagaagga cgactgccaa gagcaccgtt aatcgagtct tattagctta tgcttaacct    60
tcgagatacc gatacgataa cgagaggcgt aaccaaacat ctcagagcag aacggcgaga   120
caacgt                                                              126

<210> SEQ ID NO 67
<211> LENGTH: 126
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3 of DX-Parallelogram (PDX-E-E)

<400> SEQUENCE: 67
ggtcaactgt agcaatgccg cttgacatac gctattgtgt gtcgaggacc gttcgtcagc    60
tcggtagttg ccttacagaa ctccgccgaa acgaaaggtg gtcagtacga attacgcata   120
gtgcga                                                              126

<210> SEQ ID NO 68
<211> LENGTH: 126
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4 of DX-Parallelogram (PDX-E-E)

<400> SEQUENCE: 68
tccagagcga tgcagagtta ttatgttata ttcctacata gaacctctgt tgatatagaa    60
tagatgctca acgatgtcag gtctacgagg tggatctaca ctaaatgagc ttcggctcaa   120
tccaag                                                              126

<210> SEQ ID NO 69

```
<211> LENGTH: 64
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5 of DX-Parallelogram (PDX-E-E)

<400> SEQUENCE: 69
ttgctggagt ctaccatata gtggataatc cgtaggattc gatgcggtac attccatgaa      60
cacg                                                                   64

<210> SEQ ID NO 70
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6 of DX-Parallelogram (PDX-E-E)

<400> SEQUENCE: 70
gatagccgta tccgtgagat caccgacaga cttgcggagc gtcaatagac gagtgcctag      60
atg                                                                    63

<210> SEQ ID NO 71
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7 of DX-Parallelogram (PDX-E-E)

<400> SEQUENCE: 71
cgcaggtaat aggactgatg gtggctcctc cgtcgcatta tt                         42

<210> SEQ ID NO 72
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8 of DX-Parallelogram (PDX-E-E)

<400> SEQUENCE: 72
aaggcggcta gtcgccaact caccaatacg ttggacagcc tc                         42

<210> SEQ ID NO 73
<211> LENGTH: 83
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9 of DX-Parallelogram (PDX-E-E)

<400> SEQUENCE: 73
cttcttgaac caggttgtac gcaaactcct tgatgctata caccactcta atcacttgag      60
actggtcacg atccgctcat gta                                              83
```

<210> SEQ ID NO 74
<211> LENGTH: 85
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10 of DX-Parallelogram (PDX-E-E)

<400> SEQUENCE: 74
agagaatggt tcgctgcact agaggaggta cggttatgta cgtggcttag ttaccacgct    60
ggtctcctta ataccaggaa gactt    85

<210> SEQ ID NO 75
<211> LENGTH: 63
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 11 of DX-Parallelogram (PDX-E-E)

<400> SEQUENCE: 75
gcctcagata gtaccagacg ccaggtagct cttcaacgct tgtggcatac tctccattag    60
tat    63

<210> SEQ ID NO 76
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 12 of DX-Parallelogram (PDX-E-E)

<400> SEQUENCE: 76
catacgtgtg ccgtgcggtt gcgaaatcaa gtagtagata cacctaacgt gctgccgacc    60
gc    62

<210> SEQ ID NO 77
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 13 of DX-Parallelogram (PDX-E-E)

<400> SEQUENCE: 77
tatgagtgac gcacctatta    20

<210> SEQ ID NO 78
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 14 of DX-Parallelogram (PDX-E-E)

<400> SEQUENCE: 78
tctaagacgt tgttagactc                                                  20

<210> SEQ ID NO 79
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 15 of DX-Parallelogram (PDX-E-E)

<400> SEQUENCE: 79
ttgacctcgc actggatacg                                                  20

<210> SEQ ID NO 80
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 16 of DX-Parallelogram (PDX-E-E)

<400> SEQUENCE: 80
tctggacttg gatgactagc                                                  20

<210> SEQ ID NO 81
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 17 of DX-Parallelogram (PDX-E-E)

<400> SEQUENCE: 81
cagcaagagg ctgtgtcgtc ct                                               22

<210> SEQ ID NO 82
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 18 of DX-Parallelogram (PDX-E-E)

<400> SEQUENCE: 82
cctgcggcgg tcggtcatta ct                                               22

<210> SEQ ID NO 83
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 19 of DX-Parallelogram (PDX-E-E)

<400> SEQUENCE: 83
cgccttatac taattgcatc gc                                               22

<210> SEQ ID NO 84

```
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 20 of DX-Parallelogram (PDX-E-E)

<400> SEQUENCE: 84
gctatcaata atgctgctac ag                                              22

<210> SEQ ID NO 85
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 21 of DX-Parallelogram (PDX-E-E)

<400> SEQUENCE: 85
acacaatagc gtatgtcaag cggcatgacg gaggagcctg tatagcatca aggagtttgc     60
gtacaaccac gaacggtcct cgac                                            84

<210> SEQ ID NO 86
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 22 of DX-Parallelogram (PDX-E-E)

<400> SEQUENCE: 86
ccgagctgtg gttcaagaag cgtgttcatt gtaaggcaac ta                        42

<210> SEQ ID NO 87
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 23 of DX-Parallelogram (PDX-E-E)

<400> SEQUENCE: 87
cgtttcggcg gagttcggaa tgtaccgcat cgaatcctac ggattatcct gatctcacat     60
gcgtaattcg tactgaccac cttt                                            84

<210> SEQ ID NO 88
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 24 of DX-Parallelogram (PDX-E-E)

<400> SEQUENCE: 88
tggttacgcc tctcgttaca ctcgtctatt gacgctccgc aagtctgtcg gactatatgg     60
ctcgccgttc tgctctgaga tgtt                                            84
```

```
<210> SEQ ID NO 89
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 25 of DX-Parallelogram (PDX-E-E)

<400> SEQUENCE: 89
tcgaaggtcg aaccattctc tcatctaggt cgtatcggta tc                           42

<210> SEQ ID NO 90
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 26 of DX-Parallelogram (PDX-E-E)

<400> SEQUENCE: 90
agactcgatt aacggtgctc ttggcaccaa cgtattggac gtacataacc gtacctcctc        60
tagtgcagta agcataagct aata                                               84

<210> SEQ ID NO 91
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 27 of DX-Parallelogram (PDX-E-E)

<400> SEQUENCE: 91
ccacctcgta gacctgtggt attaaggaga ccagcgtggt aactaagcct gagttggctg        60
agccgaagct catttagtgt agat                                               84

<210> SEQ ID NO 92
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 28 of DX-Parallelogram (PDX-E-E)

<400> SEQUENCE: 92
tctattctgg cacacgtatg aagtcttcca catcgttgag ca                           42

<210> SEQ ID NO 93
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 29 of DX-Parallelogram (PDX-E-E)

<400> SEQUENCE: 93
tatgtaggaa tataacataa taactcggag agtatgcctg tatctactac ttgatttcgc        60
```
aaccgcacat atcaacagag gttc                                              84

<210> SEQ ID NO 94
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 30 of DX-Parallelogram (PDX-E-E)

<400> SEQUENCE: 94
acgcctgcaa gctagattac gaagtacagc acgttaggac aagcgttgaa gagctacctg       60
gcgtctggct gcgaagatgt attc                                              84

<210> SEQ ID NO 95
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 31 of DX-Parallelogram (PDX-E-E)

<400> SEQUENCE: 95
ggcggtgtta ctatctgagg ctacatgagt cagcagttac at                          42

<210> SEQ ID NO 96
<211> LENGTH: 84
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 32 of DX-Parallelogram (PDX-E-E)

<400> SEQUENCE: 96
agagaacatc atcggcgtcg gatcgtgacc agtctcaagt gattagagtg gaccatcagt       60
gtgaactgtt gtgcaaggaa cttc                                              84

<210> SEQ ID NO 97
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 1 of 3D DX-Triangle

<400> SEQUENCE: 97
cgacgagcat caccatgaac                                                   20

<210> SEQ ID NO 98
<211> LENGTH: 46
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 2 of 3D DX-Triangle

<400> SEQUENCE: 98
gcgtgttcat ggacgaacga ccagtggtag tgagacctgt catacg        46

<210> SEQ ID NO 99
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 3 of 3D DX-Triangle

<400> SEQUENCE: 99
tacagtagat cagaatggac tggtcgttcg tggttctacg ct        42

<210> SEQ ID NO 100
<211> LENGTH: 73
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 4 of 3D DX-Triangle

<400> SEQUENCE: 100
gtcgctatgg tcctgaacta ctcgctcaat cgcctgtatc gtgaatctac tgtaagcgta        60
gaacctgatg ctc        73

<210> SEQ ID NO 101
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 5 of 3D DX-Triangle

<400> SEQUENCE: 101
gatgagtctg tggtctcact acctgtctcg caccaagtcg ca        42

<210> SEQ ID NO 102
<211> LENGTH: 81
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 6 of 3D DX-Triangle

<400> SEQUENCE: 102
gctcctgcga gacaccattc tgccgtattc ggacatagtc accgttgtac cgacgtagga        60
cgtactcacc agctaaacgc t        81

<210> SEQ ID NO 103
<211> LENGTH: 73
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 7 of 3D DX-Triangle

<400> SEQUENCE: 103

```
gagcggcttg aggacagact catctgcgac ttggacactg cacgctctac attgactgag      60
cacggactcg acc                                                        73
```

<210> SEQ ID NO 104
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 8 of 3D DX-Triangle

<400> SEQUENCE: 104

```
gatgcgtatg acacctcaag cc                                              22
```

<210> SEQ ID NO 105
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 9 of 3D DX-Triangle

<400> SEQUENCE: 105

```
tacggtcacg atacaccgaa                                                 20
```

<210> SEQ ID NO 106
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 10 of 3D DX-Triangle

<400> SEQUENCE: 106

```
cgagtagttc accttgcttc gcctgactat gtggcgattg ag                        42
```

<210> SEQ ID NO 107
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 11 of 3D DX-Triangle

<400> SEQUENCE: 107

```
cacgagatgt tacaacggac taggtcgccg tggtcttgcc ta                        42
```

<210> SEQ ID NO 108
<211> LENGTH: 46
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 12 of 3D DX-Triangle

<400> SEQUENCE: 108

```
gcagcacagc ggacggcgac ctagtggcga agcaaggact tcatcg                    46
```

<210> SEQ ID NO 109
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 13 of 3D DX-Triangle

<400> SEQUENCE: 109
acgccgatga agtggaccat ag                                              22

<210> SEQ ID NO 110
<211> LENGTH: 73
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 14 of 3D DX-Triangle

<400> SEQUENCE: 110
ctacgatggc acctggctac agattagata tgcctgcatg tcagacatct cgtgtaggca    60
agacctgcta ttg                                                       73

<210> SEQ ID NO 111
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 15 of 3D DX-Triangle

<400> SEQUENCE: 111
gtagcaatag caccgctgtg                                                 20

<210> SEQ ID NO 112
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 16 of 3D DX-Triangle

<400> SEQUENCE: 112
gtcggctgac atgcacctac                                                 20

<210> SEQ ID NO 113
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 17 of 3D DX-Triangle

<400> SEQUENCE: 113
atctgtagcc accgattaca tcctgagtac gtggcatatc ta                       42

<210> SEQ ID NO 114

```
<211> LENGTH: 42
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 18 of 3D DX-Triangle

<400> SEQUENCE: 114
caatgtagag ttagctggac gcctatcaac accgtgctca gt                           42

<210> SEQ ID NO 115
<211> LENGTH: 46
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 19 of 3D DX-Triangle

<400> SEQUENCE: 115
catcgagctt cctgttgata ggcgtggatg taatcggacc ttatcc                       46

<210> SEQ ID NO 116
<211> LENGTH: 22
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 20 of 3D DX-Triangle

<400> SEQUENCE: 116
ctgcggataa ggtggtgcca tc                                                 22

<210> SEQ ID NO 117
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 21 of 3D DX-Triangle

<400> SEQUENCE: 117
agtgtggagc agcgtcgtgc                                                    20

<210> SEQ ID NO 118
<211> LENGTH: 20
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: Strand 22 of 3D DX-Triangle

<400> SEQUENCE: 118
gctcggtcga gtggaagctc                                                    20

<210> SEQ ID NO 119
<211> LENGTH: 20
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<223> OTHER INFORMATION: Strand 1 of DX-Parallelogram (PDX-E-O)

<400> SEQUENCE: 119
gcgtagatgg caccacgtac                                               20

<210> SEQ ID NO 120
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 2 of DX-Parallelogram (PDX-E-O)

<400> SEQUENCE: 120
cactggtatt gttagactct                                               20

<210> SEQ ID NO 121
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 3 of DX-Parallelogram (PDX-E-O)

<400> SEQUENCE: 121
tcgttgtaag ctggctacta                                               20

<210> SEQ ID NO 122
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 4 of DX-Parallelogram (PDX-E-O)

<400> SEQUENCE: 122
tcgtagttcg atgaagcact                                               20

<210> SEQ ID NO 123
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 5 of DX-Parallelogram (PDX-E-O)

<400> SEQUENCE: 123
gtagtacagt cgtgactatc at                                            22

<210> SEQ ID NO 124
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 6 of DX-Parallelogram (PDX-E-O)
```

```
<400> SEQUENCE: 124
atggagttct cggtcaacgt ct                                                      22

<210> SEQ ID NO 125
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 7 of DX-Parallelogram (PDX-E-O)

<400> SEQUENCE: 125
gtcgagtgtg aattgattac ct                                                      22

<210> SEQ ID NO 126
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 8 of DX-Parallelogram (PDX-E-O)

<400> SEQUENCE: 126
gcagcggaga tgctgaacgt gc                                                      22

<210> SEQ ID NO 127
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 9 of DX-Parallelogram (PDX-E-O)

<400> SEQUENCE: 127
ccatgtacgt ggacatagcg tggcgttagg ctcgcatctc cg                                 42

<210> SEQ ID NO 128
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 10 of DX-Parallelogram (PDX-E-O)

<400> SEQUENCE: 128
cgacagtgct tcgctaggac accgttcgcc aggacgactg ta                                 42

<210> SEQ ID NO 129
<211> LENGTH: 61
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 11 of DX-Parallelogram (PDX-E-O)

<400> SEQUENCE: 129
acgagcacgt tcaataatgc tatcactctc caaatcatta ggattaagca ccataacgtc             60
``` a                                                              61

<210> SEQ ID NO 130
<211> LENGTH: 87
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 12 of DX-Parallelogram (PDX-E-O)

<400> SEQUENCE: 130
gtcttgttgt tgcaccgtcc aagcagcctt actcacaact cgtgcgacct tcgtatattt    60
agaagtaatg gttcggttct gccatct                                       87

<210> SEQ ID NO 131
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 13 of DX-Parallelogram (PDX-E-O)

<400> SEQUENCE: 131
ctacagagtc taccatgaag tggcattgtg cgtcttgat                           39

<210> SEQ ID NO 132
<211> LENGTH: 55
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 14 of DX-Parallelogram (PDX-E-O)

<400> SEQUENCE: 132
ggagccgtgg ctctcatctc gaacgccgac tcaaatgaca ggcttatagc ttaca         55

<210> SEQ ID NO 133
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 15 of DX-Parallelogram (PDX-E-O)

<400> SEQUENCE: 133
ctgctagtag ccgtcacctc accgcaccta cgtta                               35

<210> SEQ ID NO 134
<211> LENGTH: 59
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 16 of DX-Parallelogram (PDX-E-O)

<400> SEQUENCE: 134
gtataggaag gcacatatct aactgtggaa gcaaactctt ggtgtgcaga gacaatacc     59

<210> SEQ ID NO 135
<211> LENGTH: 93
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 17 of DX-Parallelogram (PDX-E-O)

<400> SEQUENCE: 135
agtgatgata gtctgttatc tcatgccgtt tatccgccag taccaatgta gagattgtag    60
atcgtgtaag gtagtggttg ccgcatggaa cta                                 93

<210> SEQ ID NO 136
<211> LENGTH: 55
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 18 of DX-Parallelogram (PDX-E-O)

<400> SEQUENCE: 136
gattcttagt gacacatcgg aggaatgcgt tgaatcggaa atggtcaatc gaact          55

<210> SEQ ID NO 137
<211> LENGTH: 60
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 19 of DX-Parallelogram (PDX-E-O)

<400> SEQUENCE: 137
acgcagacgt tgatattccg taacatagga ccaatcacag ctcgataatc ggtaagcaag     60

<210> SEQ ID NO 138
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 20 of DX-Parallelogram (PDX-E-O)

<400> SEQUENCE: 138
ttggaggtcg aatgtggtct atgatccatt cacact                              36

<210> SEQ ID NO 139
<211> LENGTH: 61
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 21 of DX-Parallelogram (PDX-E-O)

<400> SEQUENCE: 139
agcaaggtaa tcagaggcgg ctgtctagta cggatgttcg gctggagcta cactctattc     60
t                                                                    61

<210> SEQ ID NO 140
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 22 of DX-Parallelogram (PDX-E-O)

<400> SEQUENCE: 140
gactgcgtcg atcaccgacc atcctgccga gaact             35

<210> SEQ ID NO 141
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 23 of DX-Parallelogram (PDX-E-O)

<400> SEQUENCE: 141
aatagtagaa cacaagttaa tacgcttaac ctaaggatag gtatcagtga agatcgcaat    60
cc                                                                  62

<210> SEQ ID NO 142
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 24 of DX-Parallelogram (PDX-E-O)

<400> SEQUENCE: 142
agaccgtaca agctctggtt atgcaattag cgttgcggcg actatgcact tactgccttg    60
gc                                                                  62

<210> SEQ ID NO 143
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 25 of DX-Parallelogram (PDX-E-O)

<400> SEQUENCE: 143
ttaagtacat taacacctgg aatcgctcct caggagtgag acgaggtcat acttgcatcc    60
ag                                                                  62

<210> SEQ ID NO 144
<211> LENGTH: 62
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 26 of DX-Parallelogram (PDX-E-O)

<400> SEQUENCE: 144

```
ggttactgga gtatctgaac ataccgccga taagtaggat acgatattgc tggaccgctc    60
ac                                                                   62

<210> SEQ ID NO 145
<211> LENGTH: 130
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 27 of DX-Parallelogram (PDX-E-O)

<400> SEQUENCE: 145
tgatagcatt atgagcctaa cgcctgcaac aacaagactg acgttatgga ctgataccta    60
tccttaggtt aagcgtatta ccacggctcc atcaagacgc acaatgcctg aggtgacata   120
agcctgtcat                                                          130

<210> SEQ ID NO 146
<211> LENGTH: 80
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 28 of DX-Parallelogram (PDX-E-O)

<400> SEQUENCE: 146
ttgagtcggc gttcgagatg agagacttgt gttctactat tggattgcga tcttctgctt    60
aatcctaatg atttggagag                                                80

<210> SEQ ID NO 147
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 29 of DX-Parallelogram (PDX-E-O)

<400> SEQUENCE: 147
ttgcttccac agttagatat agagcttgta cggtctgcca aggcagtaag ttacattggt    60
actggcggat aaacgg                                                    76

<210> SEQ ID NO 148
<211> LENGTH: 134
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 30 of DX-Parallelogram (PDX-E-O)

<400> SEQUENCE: 148
catgagataa cacctggcga acggactacc ttacacgatc tacaatctcg catagtcgcc    60
gcaacgctaa ttgcataacc gtgccttcct atactaacgt aggtgcggac ttcatggctc   120
tgcacaccaa gagt                                                     134

<210> SEQ ID NO 149
```

```
<211> LENGTH: 129
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 31 of DX-Parallelogram (PDX-E-O)

<400> SEQUENCE: 149
gacagccgcc tcggatcata gacctgatcg acgcagtcag aatagagtgc ctcgtctcac      60
tcctgaggag cgattccagg actaagaatc tagttccatg cggcaacctg tcctagctga     120
ccatttccg                                                             129

<210> SEQ ID NO 150
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 32 of DX-Parallelogram (PDX-E-O)

<400> SEQUENCE: 150
attcaacgca ttcctccgat gtgtctgtta atgtacttaa ctggatgcaa gtatgatagc      60
tccagccgaa catccgtact a                                                81

<210> SEQ ID NO 151
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 33 of DX-Parallelogram (PDX-E-O)

<400> SEQUENCE: 151
tacttctaaa tatacgaagg tcgcaagata ctccagtaac cgtgagcggt ccagcagatt      60
atcgagctgt gattggtcct a                                                81

<210> SEQ ID NO 152
<211> LENGTH: 129
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Strand 34 of DX-Parallelogram (PDX-E-O)

<400> SEQUENCE: 152
tgttacggaa tacaggatgg tcggacattc gacctccaac ttgcttacca tatcgtatcc      60
tacttatcgg cggtatgttc cgagttgtga gtaaggctgc ttggacggac gctatgtgaa     120
ccgaaccat                                                             129
```

POLYGONAL NANOSTRUCTURES OF POLYNUCLEIC ACID MULTI-CROSSOVER MOLECULES AND ASSEMBLY OF LATTICES BASED ON DOUBLE CROSSOVER COHESION

CROSS-REFERENCE TO RELATED APPLICATIONS

The present application claims the benefit of priority under 35 U.S.C. §119(e) from provisional U.S. application No. 60/578,306, Jun. 10, 2004, the entire contents of which are incorporated by reference.

GOVERNMENT LICENSE RIGHTS

The experiments reported in this application were supported in part by: the National institute of General Medical Sciences, grant no. GM-29554; the Office of Naval Research, grant no. N00014-98-1-0093; the National Science Foundation, grant nos. DMI-0210844, EIA-0086015, DMR-01138790 and CTS-0103002; and DARPA/AFSOR, grant no. F30602-01-2-0561. The U.S. Government has a paid-up license in this invention and the right in limited circumstances to require the patent owner to license others on reasonable terms as provided for by the terms of the above grants.

BACKGROUND OF THE INVENTION

1. Field of the Invention

The present invention relates to polynucleic acid nanostructures and lattices.

2. Description of the Related Art

The control of the structure of matter on the finest possible scale requires the successful design of both stiff intramolecular motifs and robust intermolecular interactions. Previous motifs used to design 2D crystalline arrays have included the double crossover (DX) (Fu et al., 1993; Winfree et al., 1998), triple crossover (TX) (LaBean et al., 2000), the DNA parallelogram (Mao et al., 1999), and the four-by-four structure (Yan et al., 2003). These motifs have been used to produce 2D crystalline arrays lacking symmetry or with twofold symmetry (Seeman, 2003). By contrast, all previous attempts to produce trigonal or hexagonal arrays have met with failure or produced only very tiny structures. Given the inherent rigidity of triangles, the importance of trigonal motifs in nature (Kappraff et al., 1990), it is key to solve this problem. The flexibility of 3-arm junctions was discovered in the first attempt to assemble a hexagonal lattice (Ma et al., 1986). Triangles built from bulged 3-arm junctions (Liu et al., 1994) demonstrated cyclic closure with trimers and above, not just from the hexamers one would have expected (Qi et al., 1996). Triangles whose edges were flanked by coplanar helices derived from DX molecules behaved in a similar fashion (Yang et al., 1998).

Brun et al. (2004), reported experimental evidence of two new complexes, quadruple crossovers and triangles, where atomic force microscopy images (AFM) show that the triangles are capable of hexagonally tiling the plane. However, the triangular units used by Brun et al. to form a hexagonal lattice have single nucleic acid helices for its edge and are not robust, as the AFM image of the lattice formed appears to show that some pentagons and squares are present in the lattice.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a polynucleic acid structure which is composed of one or more polygonal units. Each polygonal unit has, as its edges, connected nucleic acid multi-crossover domains. Each edge of a polygonal unit has at least one free end (extension of the edge) with two parallel nucleic acid helices terminating in a double cohesive (sticky) end.

The invention also provides a method for producing the polynucleic acid structure according to the present invention which involves mixing single stranded polynucleotides, each being designed to be self-complementary and/or complementary to another single stranded polynucleotide so as to be capable of self-annealing into a polygonal unit, and annealing the mixture after heat denaturation to form the polygonal unit. The method may further involve the self-assembly of an array of polygonal units by annealing complementary exposed cohesive ends on the polygonal units.

BRIEF DESCRIPTION OF THE DRAWINGS

FIGS. 1A-1E illustrate the following motifs: the DX motif (FIG. 1A); the bulged junction triangle (FIG. 1B); the DX triangle (FIG. 1C); a trigonal arrangement of six DX triangles of two different species (FIG. 1D); a schematic trigonal lattice of the two triangles shown in FIG. 1D (FIG. 1E).

FIGS. 2A and 2B schematically show the arrangement and nucleotide sequences of two DNA DX triangles, DTX-A (FIG. 2A; SEQ ID NOs:1-13) and DTX-B (FIG. 2B; SEQ ID NOs:1-2, 4, 6, 9, 11, and 13-19).

FIG. 3A shows a pair of 2D arrays. The honey-comb nature of the arrays are evident. FIG. 3B is a zoom (enlargement) of the array shown on the right in FIG. 3A. FIG. 3C is a zoom (enlargement) of another array. FIG. 3D shows an image containing two stacked arrays, virtually complete on the lower right, partial on the upper left. FIG. 3E is a zoomed (enlarged) image containing 15 DX triangles. FIG. 3F is a further zoom (enlargement) of FIG. 3E showing six complete triangles, similar to the arrangement in FIG. 1D, and with a center-center hexagon outline superimposed.

FIGS. 7A and 8B show illustrations of a 6-helix bundle down its central axis (FIG. 7A), and along its side (FIG. 7B). It can be seen that it is just a fused set of DX molecules, at 120° to each other.

FIG. 10B has one side (closest to the reader) in a similar orientation as in FIG. 10A, but the other two sides have been added, including one side viewed edge on. It is evident that this motif spans 3-space. FIG. 10C is a top view of the trigonal motif.

DETAILED DESCRIPTION OF THE INVENTION

Figure 1E:
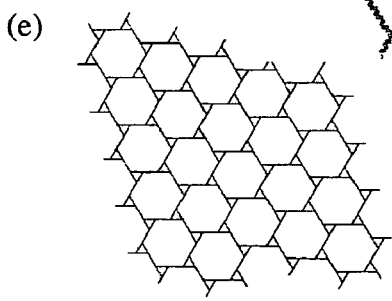

The polynucleic acid structures of the present invention are polynucleic acids that are assembled to form branched multimers of repeating units composed at least partially of multi-crossover molecules in accordance with the method of the present invention.

A plurality of multi-crossover molecules, which form a basic unit of a robust nucleic acid motif, such as a nucleic acid triangle, are assembled from single stranded oligonucleotides or polynucleotides to produce the polynucleic acid unit molecules of the present invention. Similarly, more complex polynucleic acid structures of the present invention having two dimensional or three dimensional periodic lattices with symmetrical intermolecular contacts (translational symmetry) are assembled from basic units of linked multi-crossover molecules.

The term "robust" as used herein is meant to refer to producing the designed structure exclusively, and no others. This applies not only to motifs but also to structures such as arrays and lattices. For instance, if a DX triangle is designed, then its component strands will only self-assembled into the designed DX triangle motif/structure.

DNA molecules containing two crossover sites between helical domains have been widely suggested as intermediates in recombination processes involving double stranded breaks. Accordingly, "double crossover molecules" are those nucleic acid molecules containing two branched junctions (Holliday junctions corresponding to the crossover sites) linked together by ligating two of their double helical arms. By branched junction (arms) is meant a point from which three or more helices (arms) radiate.

There are five isomers of double crossover molecules (Fu et al., 1993), which fall into two broad classes of molecules differentiated by the relative orientations, parallel (DP) or antiparallel (DA), of their helix axes. As parallel double helical molecules are usually not well behaved, antiparallel isomers of double crossover molecules are the preferred building block components intended to be used in the present invention. However, parallel double helical molecules may be suitable as well.

The present inventors have now developed a new motif, the DX triangle, which is capable of forming a trigonal array. This motif is derived by combining the DX motif (FIG. 1A) with the bulged triangle motif (FIG. 1B). The resulting motif is illustrated in FIG. 1C. The DX molecule has been shown to be about twice as stiff as conventional linear duplex DNA (Li et al., 2002; Sa-Ardyen et al., 2003). Thus, one might expect that this doubly-thick triangle would be more rigid than the simple bulged junction triangle. In addition, the DX triangle is capable of a double intermolecular interaction that may be more robust than the single helical interactions used previously, because it is less sensitive to errors in twist. The self-assembly of a trigonal array from this motif is shown in Example 1 hereinbelow. Example 1 demonstrates that improving or stabilizing the intermolecular contacts is the key feature of the DX triangle motif that enables formation of trigonal arrays.

The DX triangle and the trigonal arrays or lattices formed from this motif as mentioned above and disclosed in Example 1 hereinbelow are preferred embodiments of the polynucleic acid structure of present invention. It is intended that the polynucleic acid structure of the present invention encompass not only DX triangle motifs and trigonal arrays/lattices formed therefrom but also other multi-crossover motifs, such as but not limited to, a skewed TX-DX triangle and a DX parallelogram disclosed in Example 2 hereinbelow, and arrays/lattices formed therefrom.

The polynucleic acid structure of the present invention is composed of one or more polygonal units. When only a single polygon is present, the polygonal polynucleic acid structure is a unit building block for forming arrays and lattices, whereas plural linked polygonal units can be the array or lattice or can be used to further extend the array or lattice in two or three dimensions.

Figure 5:
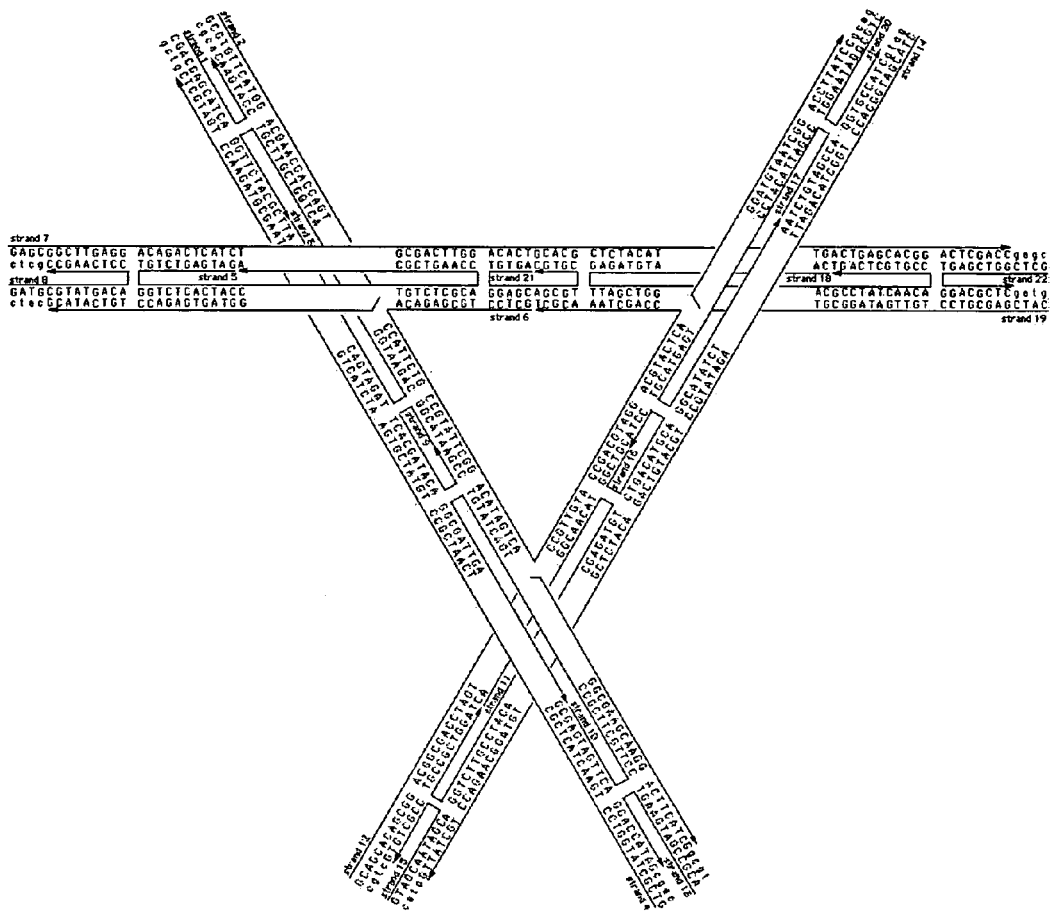
FIG. 5 schematically shows the arrangement and nucleotide sequences of 3D DX triangle (SEQ ID NOs: 97-118).

Each polygonal unit has, as its edges, connected nucleic acid multi-crossover domains. The terms "edge" or "edges" are used synonymously with the terms "side" or sides" when referring to geometrical structures such as a polygon. A polygon as used herein is a closed geometrical structure having three or more edges or sides. While a polygon is generally thought to be confined to a plane, it is intended for the purposes of the present invention to include motifs such as the three dimensional DX triangle and skewed TX-DX triangle shown in FIGS. 5, 10C and 11 (polygonal when viewed from above).

As would be recognized and appreciated by those of skill in the art, although the edges of each polygonal unit may be described as being formed by one or more nucleic acid multi-crossover molecule, it may not be possible to identify the discrete limits of individual nucleic acid multi-crossover molecules; rather, it may be more appropriate to think of connected nucleic acid multi-crossover domains forming the edges of a polygonal unit. This is more consistent with the manner in which polynucleic acid structures are produced according to the present invention, where individual nucleic acid strands self-assemble to form a polygonal unit based on sequence complementarity. Accordingly the edges are not formed as individual molecules to be linked together but rather are self-assembled as a whole into a polygonal unit.

Each edge or side of the polygonal unit has at least one free end with two parallel helices. A "free end" is intended to mean an extension of an edge beyond a vertex where one edge is connected to another edge of the polygonal unit. Each free end has at least two parallel nucleic acid double helices where at least two of the parallel helices each terminate in a cohesive or sticky end. When a free end has only two parallel helices, then the free end has a double cohesive end which can cohere with another double cohesive end that is complementary. The double cohesive ends can be the same or different cohesive ends. Each edge can alternatively have both of its ends as free ends. As another embodiment, a polygonal unit can have edges with one free end, edges with two free ends, edges with no free ends, or a combination thereof.

The nucleic acid multi-crossover domains preferably can be double or triple crossover domains or a combination thereof, such as exemplified by the skewed TX-DX triangle presented in Example 2 hereinbelow.

The polygonal unit can be any polygon that can be suitably extended from two or more of its edges to join other polygonal units and form an array or lattice. Preferably, the polygonal unit is a triangle or a parallelogram, although it is not limited to such.

A preferred embodiment of the polynucleic acid structure of the present invention is an array of triangular units linked together by complementary double cohesive ends to form a trigonal array. More preferably, the array is a trigonal array of two different triangular units. Another preferred embodiment is an array of parallelogram units linked by complementary double cohesive ends.

The present invention further provides a method for producing a polynucleic acid structure according to the present invention. This method involves synthesizing single stranded polynucleotides, each being designed to be self-complementary and/or complementary to another single stranded polynucleotide so as to be able to self anneal into a polygonal unit; mixing the single stranded polynucleotides to form a mixture of polynucleotides; heat denaturing the mixture; and annealing the heat denatured mixture of single stranded polynucleotides to form the polygonal unit.

Single stranded polypeptides are mixed together and heated at a temperature above the melting temperature or denaturation temperature of the complementary strands, e.g., 90° C., to eliminate any initial secondary structures present in the mixture, and then cooled slowly to allow the strands to anneal based on sequence complementarity.

Once the polygonal units are self-assembled, the assembled polygonal units can form arrays and lattices based on joining of double cohesive ends on polygonal units. The self-assembled, polygonal units are first heated to ensure that the double cohesive ends are exposed, and then the exposed double cohesive ends that are complementary are annealed to form an array of polygonal units. More than one polygonal unit, such as different polygonal units, can be mixed to form an array of different polygonal units.

It should also be understood that when synthesizing the single stranded oligonucleotides or polynucleotides for forming the topologically closed nucleic acid structure, the choice of sequence is substantially arbitrary, provided that strands intended to form a hairpin or to be opposite one another are complementary. It is preferable to use previously described symmetry minimization algorithms (Seeman, 1990; Seeman, 1981 and 1982) in order to optimize the sequences and incorporate the desired features while avoiding unwanted cross-hybridization or branch migration.

It should also be appreciated that the term "nucleic acid" refers to both DNA and RNA and hybrids of the two. The structure need not resemble anything which can theoretically be made from nature. A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, π, (Piccirilli et al., 1990), inosine and other derivatives of purine and pyrimidine may be used. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

A particular strand need not have a single contiguous ribose-phosphate or deoxyribose-phosphate backbone. It could be a peptide nucleic acid with a peptide backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phosphoramidite at one end. This structure has been inserted covalently instead of four T nucleotides to form a hairpin loop in a fashion similar to the nucleotides it replaces. See Mitchel J. Doktycz, Ph.D. Thesis (1991), University of Illinois, Chicago. The term "oligonucleotide", "polynucleotide" and "nucleic acid" are intended to cover all of these structures.

In nature and the field of molecular biology, double stranded DNA generally occurs in the B form. However, for the purposes of this invention it may be desirable for DNA or other double stranded polynucleotide to exist in the A, C, D or Z form. Various bases, derivations and modifications may be used to stabilize the structure in the A, C, D or Z form as well.

Three dimensional polynucleic acid structures are particularly well suited for use as a scaffolding medium since they are stiff molecules unlikely to be perturbed markedly by tethering smaller non-interactive molecules to it. Another application for this structure is in the formation of polycatenated polymers.

The structure also makes a suitable material for immobilizing enzymes and other catalysts. By employing an open design for the structure, one or more enzymes may be bound to the structure and still permit free mobility of substrates and products to and from the enzyme. Instead of binding the enzyme directly to the structure, the structure may form a cage to entrap the enzyme(s). This technique has additional advantages of not modifying the enzyme.

Conventional enzyme immobilization techniques depend on random attachment and thus the solid phase particles formed are not uniform in either activity or structure. By contrast, one can attach a predetermined number of enzymes to the polynucleotide strands being added to form a structure with a fixed number and orientation of enzymes.

The structure may be so formed to create a mesh or screen-like material. This material can be used as a filter of very precise porosity. For added strength, plural layers of mesh may be linked together or a layer may be bound to any other conventional substrate.

The structures of and produced by the present invention have numerous two dimensional and three dimensional structural uses. Because of the minute size of the structures, they have application in the field of nanotechnology.

More current uses include use as a solubilizer or stabilizer for chemicals, particularly pharmaceuticals. For example, a drug may be bound to the interior of a three dimensional polynucleic acid structure. Since DNA degrades in acidic conditions and RNA degrades in alkaline conditions, one can direct the drug to be released in whatever part of the digestive system desired.

Having now generally described the invention, the same will be more readily understood through reference to the following examples which are provided by way of illustration and are not intended to be limiting of the present invention.

EXAMPLE 1

Trigonal 2D DNA Crystals Based on Double Crossover Cohesion

Two-dimensional pseudo-hexagonal trigonal arrays have been constructed by self-assembly from DNA. The motif used is a bulged-junction DNA triangle whose edges and extensions are DNA double crossover (DX) molecules, rather than conventional DNA double helices. The experiments described below in this example were performed to establish whether the success of this system results from the added stiffness of DX molecules or the presence of two sticky ends at the terminus of each edge. Removal of one sticky end precludes lattice formation, suggesting that it is the double sticky end that is the primary factor enabling lattice formation.

Materials and Methods

The strands were synthesized by conventional phosphoramidite procedures (Caruthers, 1985), and were purified by denaturing polyacrylamide gel electrophoresis. Stoichiometric mixtures of the strands (estimated by $OD_{260}$) for each triangle were prepared separately to a concentration of 0.5 µM in a solution containing 40 mM Tris-HCl, pH 8.0, 20 mM acetic acid, 2 mM EDTA, and 12.5 mM magnesium acetate. Each mixture was cooled from 90° C. to room temperature in a 500 ml water bath over the course of 48 hrs. To form the array, the two complexes DTX-A (FIG. 2A) and DTX-B (FIG. 2B) were mixed in stoichiometric quantities, warmed to 45° C., and cooled slowly to room temperature in a thermos containing a 500 ml water bath over 24 hours; sometimes the sample was cooled another 24 hours to 16° C. Atomic Force Microscopy (AFM) imaging was performed by spotting a 5-7 µL sample drop on freshly cleaved mica, which was left to adsorb to the surface for 3 min. To remove buffer salts, 5-10 drops of double distilled water were placed on the mica, the drop was shaken off, and the sample was dried with compressed air. Imaging was performed in contact mode under 2-propanol in a fluid cell on a NanoScope IV (Digital Instruments) instrument, using commercial cantilevers with $Si_3N_4$ tips (DI).

Results

Two triangles were designed to produce a trigonal lattice arrangement when combined. The sequences (SEQ ID NOs: 1-19) of the triangles are presented in FIGS. 2A and 2B. For purposes of economy, some strands were used in both triangles. The edges of the triangles contain 65 nucleotide pairs in each of their DX helices, and they terminate in 5' sticky ends six nucleotides in length. There are four turns per edge within each triangle. The triangles are designed to cohere with each other to produce a continuous DX structure 13 double helical turns (~46 nm) in length. FIG. 1D illustrates a group of six triangles, three of each species, flanking a hexagon. The edge of the hexagon, lacking one triangle is 9 turns (~30 nm) in length; the center-to-center distance should be ~34 nm. FIG. 1E shows the way that the two DX triangles are designed to associate into pseudo-hexagonal trigonal 2D arrays. The trigonal lattice shown in FIG. 1E show an elaboration of the 6-triangle complex illustrated in FIG. 1D.

Figures 3A, 3B:
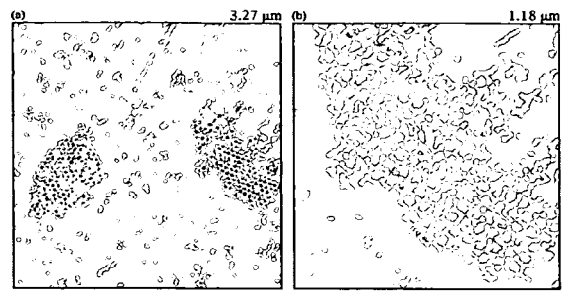
FIGS. 3A-3F present Atomic Force Microscopy (AFM) images of pseudo-hexagonal trigonal arrays. Field sizes are indicated in the upper right corners.

The triangles migrate as single bands on non-denaturing gels (data not shown). FIGS. 3A and 3F show atomic force micrographs of arrays produced by the self-assembly of the triangles.

Figures 3C, 3D:
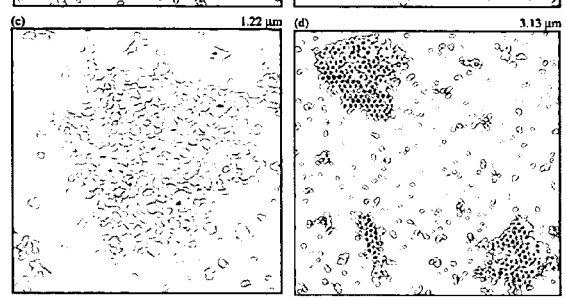
Figures 3E, 3F:
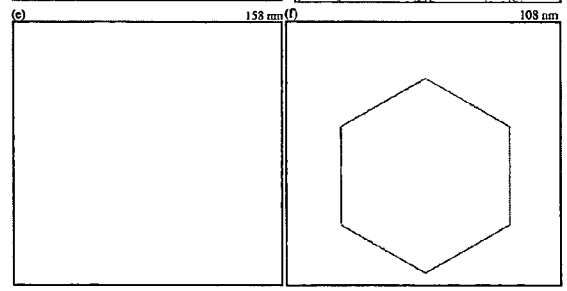

The honeycomb structure of arrangements is evident from the images shown in FIGS. 3A-3F. The quality of the lattice is evident in the images shown in FIGS. 3A-3C. The lattices have a certain tendency to stack on each other, as shown in FIG. 3D; the array in the upper left illustrates this point clearly, because the array on top is only about half the size of the array below it. Note that the arrays seem to stack over each other so that the cavities appear to be continuous between layers. The zoomed images shown in FIGS. 3E-3F demonstrate clearly the hexagonal nature of the array; the center-to-center hexagon in FIG. 3F has an edge of ~38 nm, in good agreement with the expected length.

Given the previous failures to form uniform hexagonal arrays or even hexagonal arrays at all, it is of central importance to establish which of the differences between the current system and previous systems has proved to be the key change, the greater stiffness of the DX, or the cohesion of the double sticky ends. To resolve this issue, the laboratory of the present inventors have repeated these experiments by removing the sticky (cohesive) ends from one of the helices on each of the triangles. When these modified molecules were put through the same protocols that was done with the doubly sticky-ended triangles, the lattices of the sort shown in FIGS. 3A-3F were unable to be produced. Thus, the difference is the use of double sticky (cohesive) ends.

The present inventors suspect that the previous failures were due to differences between ideal and actual twists along a single helix; two helices apparently are able to bind successfully while maintaining the orientation of the plane defined by the two helix axes of the DX edges. Nevertheless, the possibility that the flexibility of the single-helical connection contributes to the failure of those molecules to form honeycomb arrays cannot be excluded.

Thus, the substitution of DX arms for double helical arms leads to robust self-assembly in 2D. If this conclusion is correct, one ought to be able to use this approach in other motifs that have proved ineffective or difficult when used as components of 2D arrays connected by single helical sticky ends. The present inventors have tested this notion in a number of systems, and found that it is correct. The present inventors have successfully built robust 2D arrays using DX versions of a small 3D triangle (Liu et al., 2004), a 6-helix bundle (Mathieu et al., 2001), a large and unwieldy DNA parallelogram (Mao et al., 1999), and a previously unreported 3D TX motif, as described below in Example 2. The present inventors expect that the use of this form of cohesion with double sticky (cohesive) ends will prove of value both in two dimensional applications, and in three dimensional assemblies as well.

EXAMPLE 2

New Systems from DX Molecules

The first three of these new systems are 3-space spanning motifs. If one combines them along the three vectors defined by their complementary sticky end pair directions (all are connecting DX units in essence), a 3D solid will result. All three motifs behave well on non-denaturing gels, migrating as a single band.

3D DX Triangle

Figure 2A:
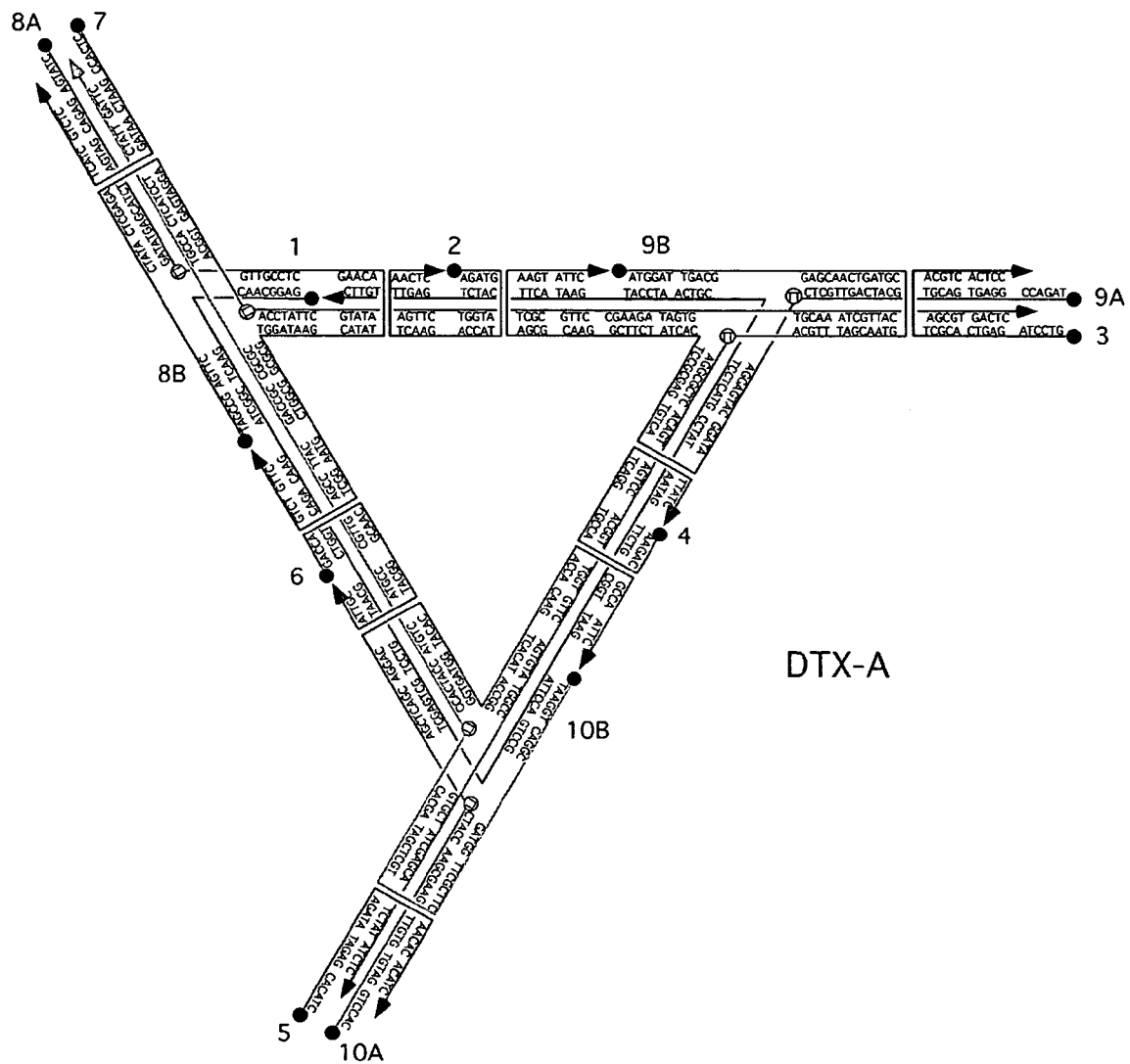
Figure 2B:
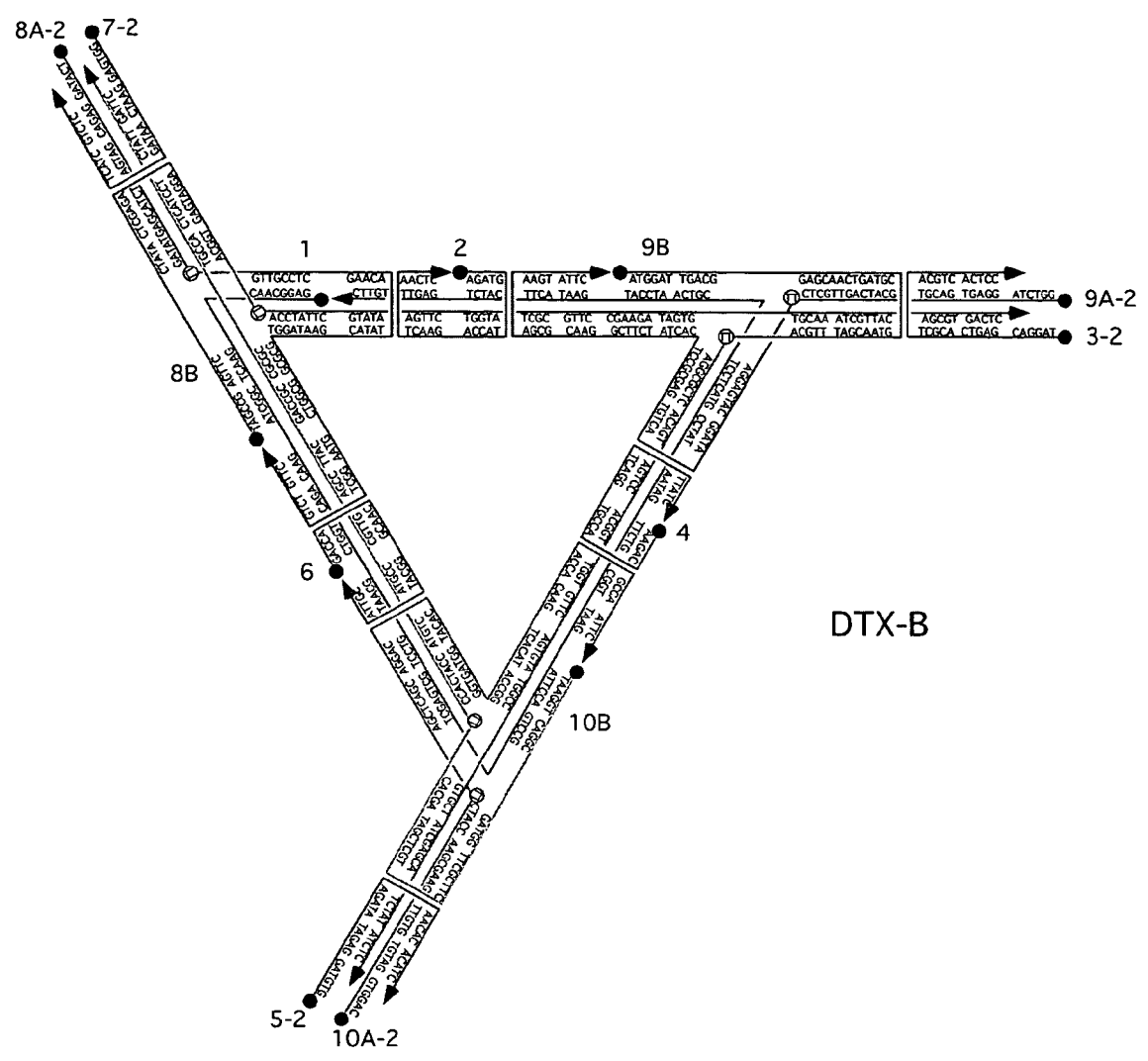
Figure 4:
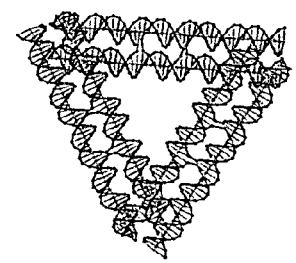
FIG. 4 is an illustration showing the 3D character of a DX triangle. Each edge consists of a DX molecule (two fused DNA double helices). Each edge is below one DX and above another; for example, the horizontal edge at the top lies above the diagonal DX on the left and below the diagonal DX on the right. The central axes of the three DX edges span 3-space.
Figure 6A:
FIGS. 6A-6C show three different sections of 2D AFM images corresponding to eliminating cohesive ends from each different direction. Note the well-formed arrays in each section, with the best array from the middle section (FIG. 5B). Dimensions flanking the images are in microns.
Figure 6B:
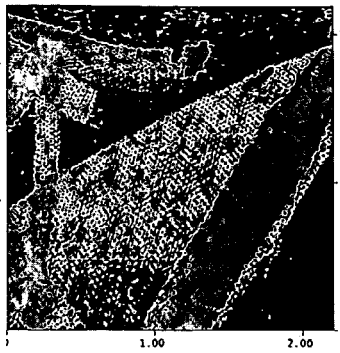
Figure 6C:
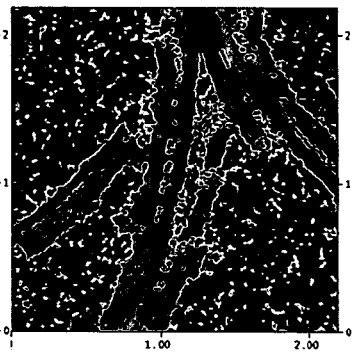

A DX triangle, different from the DX triangle of FIG. 1C and FIGS. 2A-2B, is illustrated in FIG. 4. A schematic illustration of a 3D DX triangle with double cohesive ends at the free ends (extensions) of its edges is presented in FIG. 5. A good screen for the geometrical viability of a 3D system is to eliminate one pair of cohesive ends from that system and then to see if it forms a good 2D array, as assayed by the AFM. If all three 2D sections of the system are good, it is an indication that geometrical design problems have been solved. The present inventors have been markedly successful in this regard for the 3D DX triangle, as shown in FIGS. 6A-6C.

Some tube-formation is visible in these images, likely because the DX motif selected (DAE—that has an even number of half-turns between crossovers; Fu and Seeman, 1993) tends to have internal bends; another motif (DAO—with an odd number of half-turns; Fu and Seeman, 1993) lacking this problem has also been developed. Note that the 2D arrays are rhombic, not trigonal, because one direction of propagation has been eliminated.

A Six-Helix Bundle

Figure 7A:
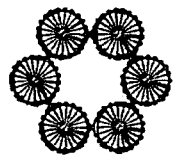
Figure 7B:
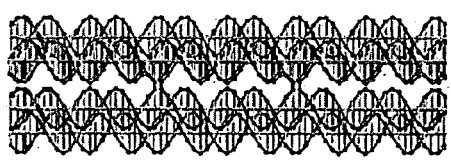
Figure 8:
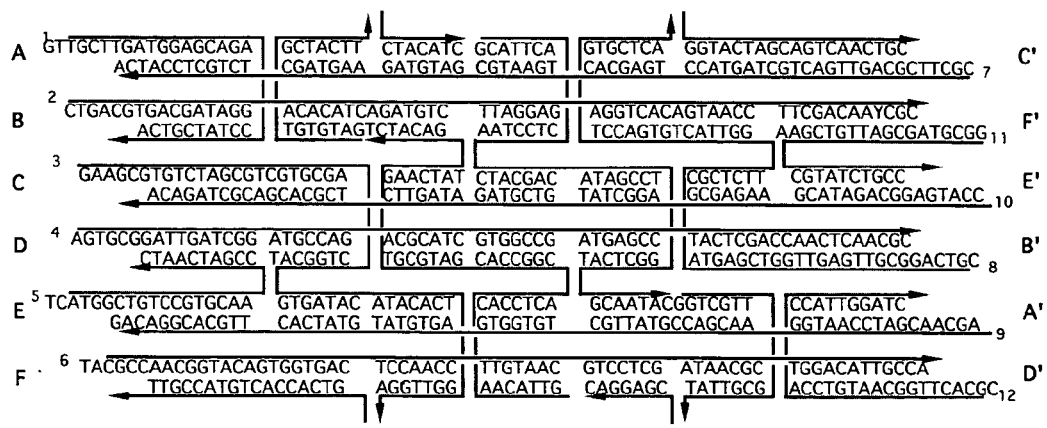
FIG. 8 schematically shows the arrangement and nucleotide sequences of the 6-helix bundle (SEQ ID NOs:20-31) presented in FIGS. 7A and 7B.

The 10.5-fold helicity of DNA (Wang, 1979; and Rhodes and Klug, 1980) means that 7- and 14-nucleotide separations between features such as crossovers rotate them by 120°. This feature was utilized to produce a 6-helix bundle of DNA (Mathieu et al., 2001), illustrated in FIGS. 7A and 7B, by combining the designed strand sequences SEQ ID NO:20-31 as shown in FIG. 8.

Figures 9A, 9B, 9C:
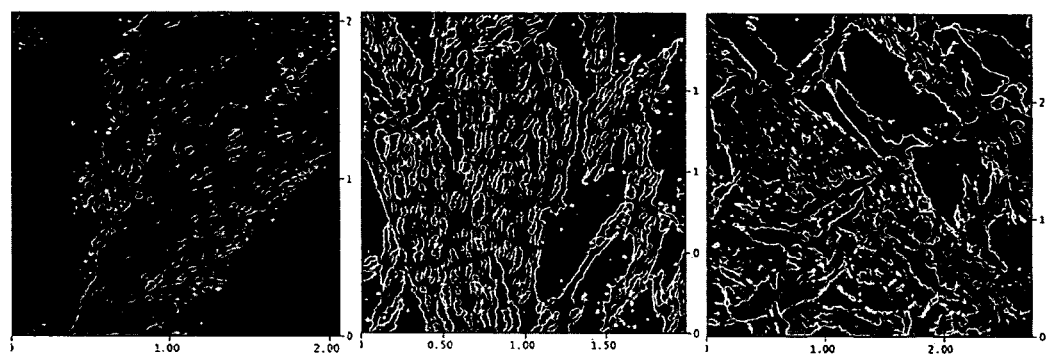
FIGS. 9A-9C are AFM images of three sets of 2D sections for the 6-helix bundle.

The laboratory of the present inventors has made arrays in each of the three directions with this motif, similar to the 3D DX triangle. The top two helices in front connect to the bottom two helices in the rear, and similarly for the other two sets. These are shown in FIGS. 9A-9C. Well defined patterns are visible, but it is clear that the overall structure of the arrays contains many faults. The faults visible in these lattices, particularly the middle one, are suspected to be the result of too few crossovers between the helices near their ends.

Skewed TX Triangle

Figures 10A, 10B, 10C:
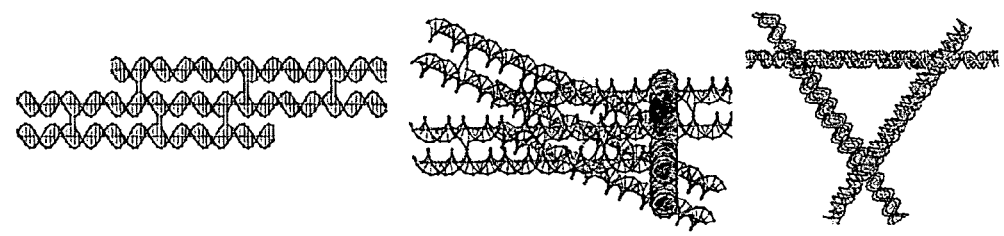
FIGS. 10A-10C show illustrations of skewed TX triangles. One side of the skewed TX triangle is shown in FIG. 10A. It is clearly made of a pair of DX ends fused by the TX motif at the center.
Figure 11:
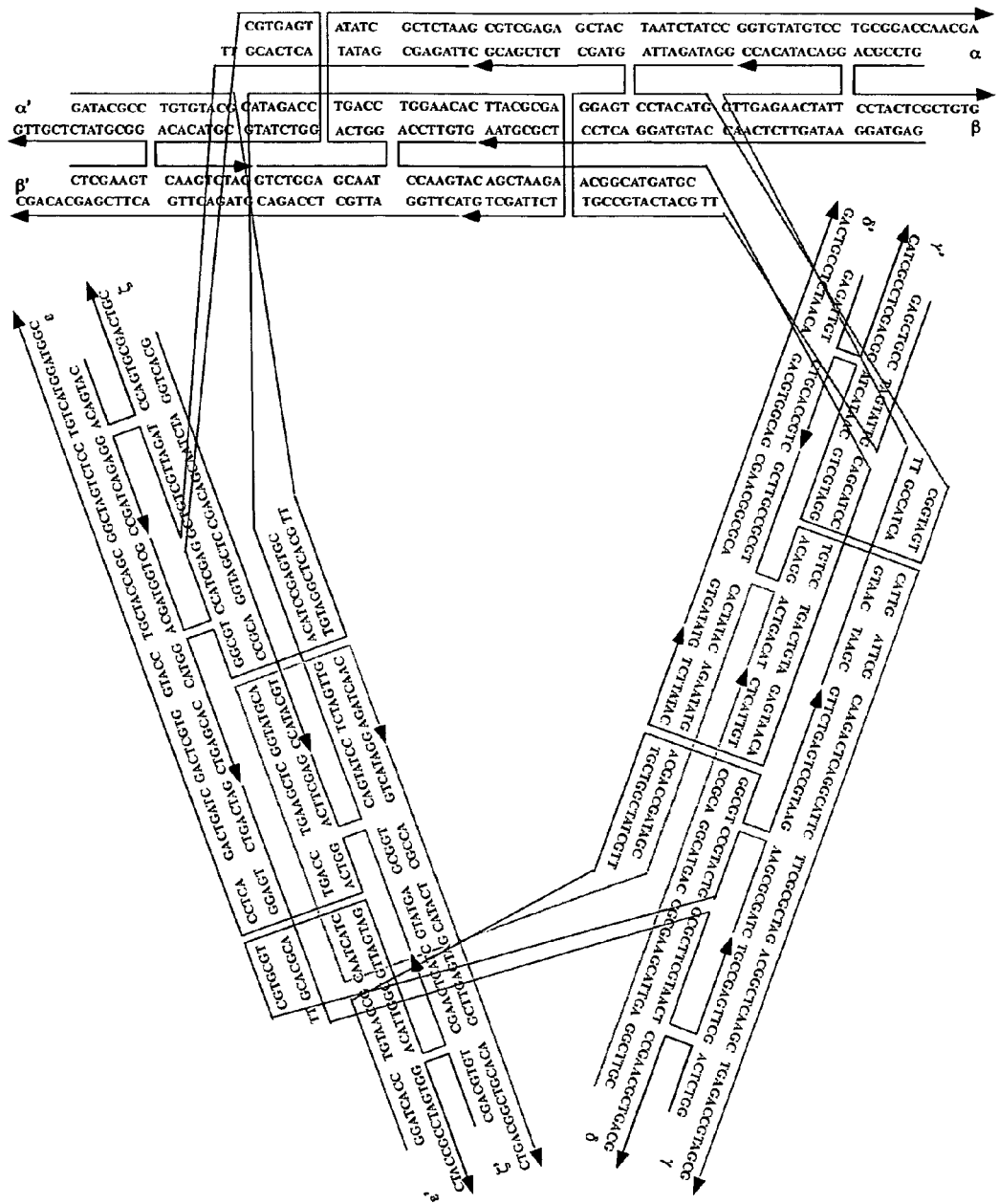
FIG. 11 schematically shows the arrangement and nucleotide sequences of the skewed TX triangle (SEQ ID NOs:32-64) presented in FIGS. 10A-10C.
Figures 12A, 12B, 12C:
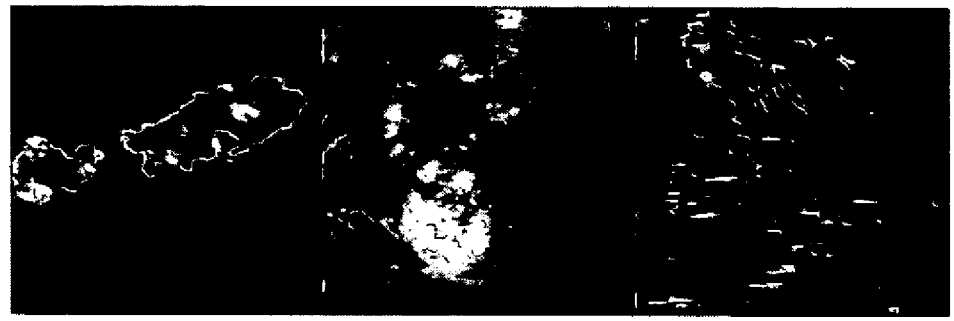
FIGS. 12A-12C are AFM images of three 2D sections of the skewed TX triangle shown in FIGS. 12A-12C. The 2D patterning is shown most clearly in FIG. 12B, whereas the other two (FIGS. 12A and 12C) are not well-formed arrays.

The skewed TX triangle motif is made up of TX molecules whose helices are extended pair-wise, as shown in FIG. 10A. Three of these molecules are put together in a skewed trigonal fashion, spanning 3-space by combining the designed strand sequences SEQ ID NOs: 32-64 (FIG. 11). The three 2D sections for this motif are shown in FIGS. 12A-12C.

DX Parallelogram

Figure 13:
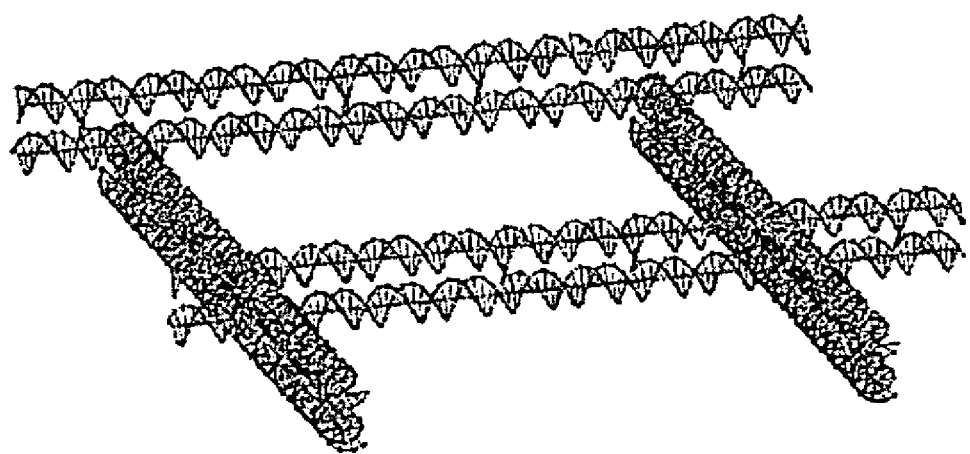
FIG. 13 shows an illustration of a DX parallelogram (PDX-E-E) with two turns beyond the vertices and 8 between them in both directions.
Figure 14:
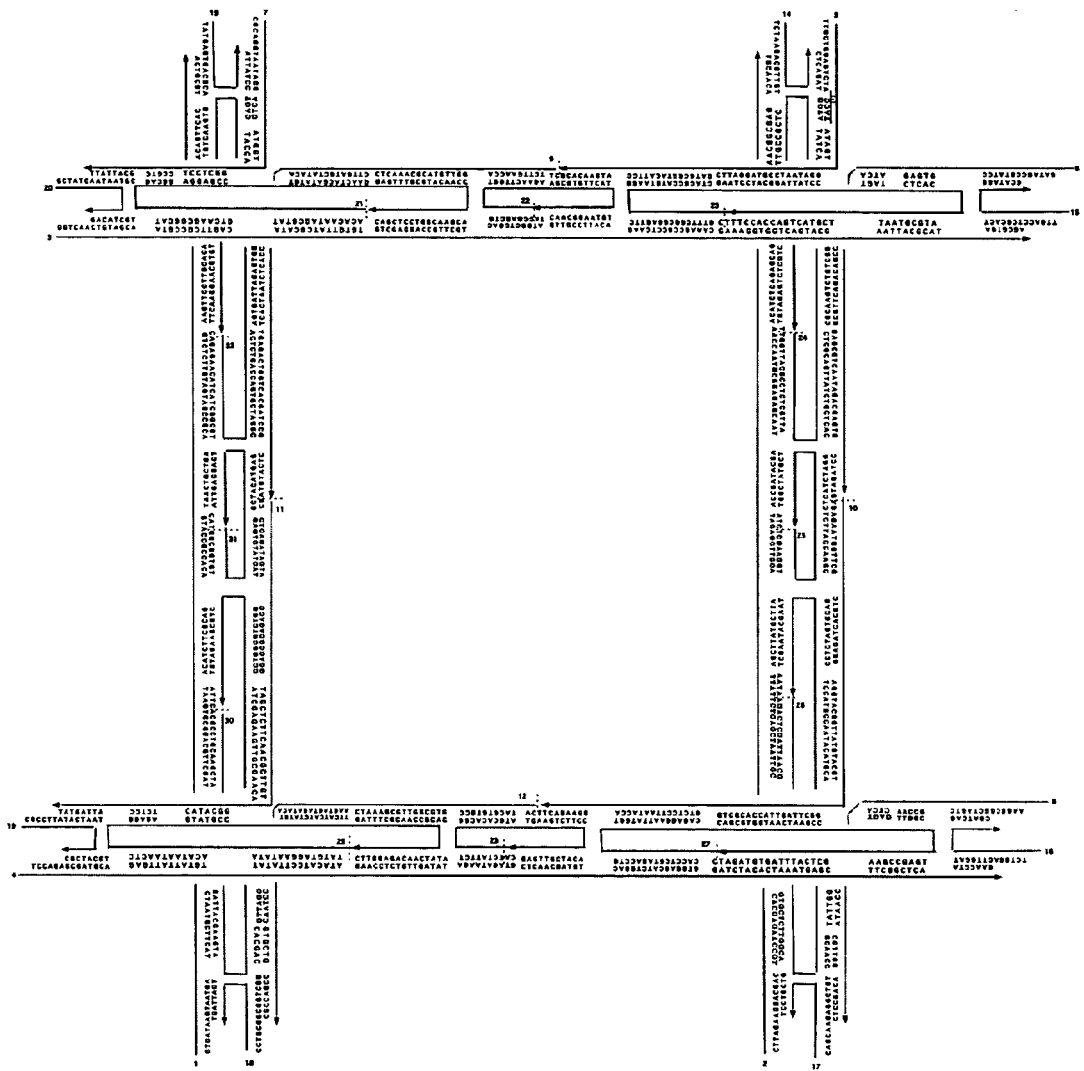
FIG. 14 schematically shows the arrangement and nucleotide sequences (SEQ ID NOs:65-96) of the DX parallelogram (PDX-E-E) presented in FIG. 13.
Figures 15A, 15B:
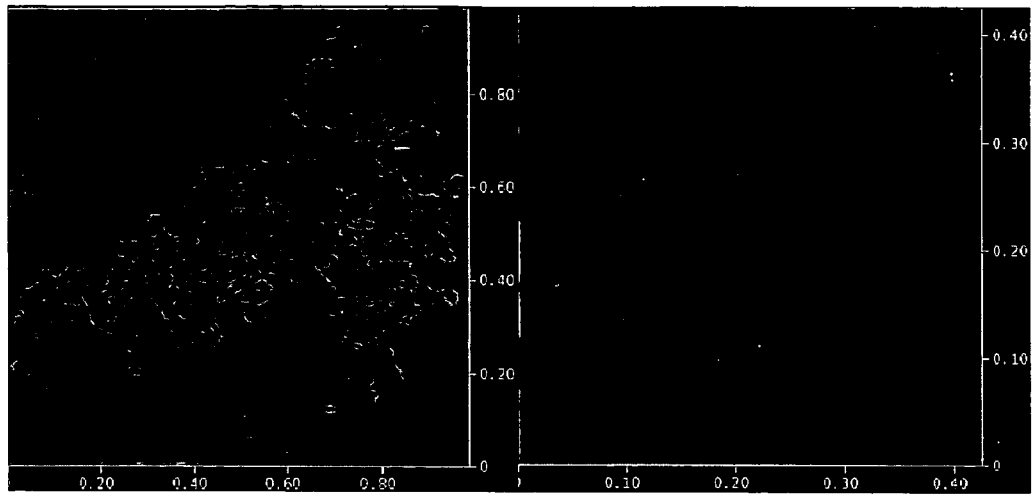
FIGS. 15A and 15B are AFM images of a view (FIG. 15A) and a zoom (FIG. 15B) of the 2D lattice formed from the motif shown in FIGS. 13 and 14.
Figure 16:
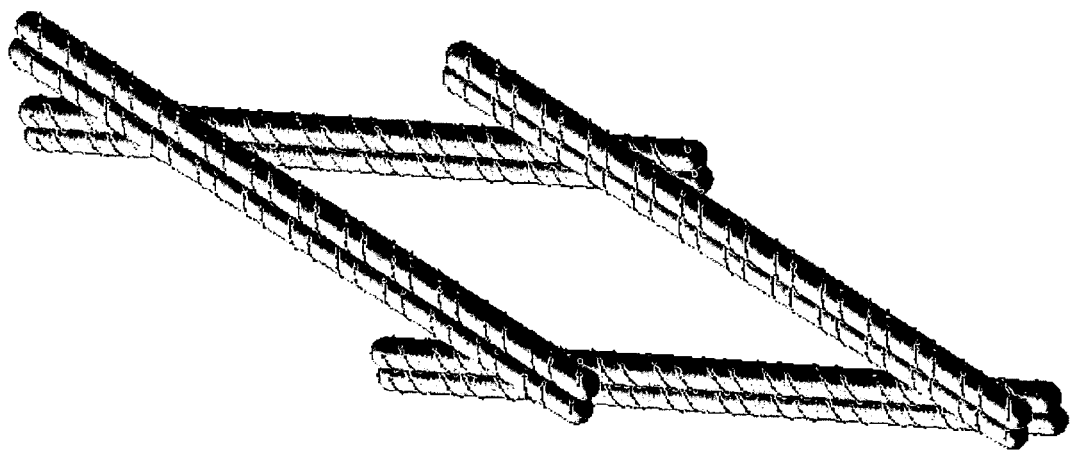
FIG. 16 shows an illustration of a DX parallelogram (PDX-E-O) with a repeating pattern of alternating even and odd numbers of half helical turns between junctions.
Figure 17:
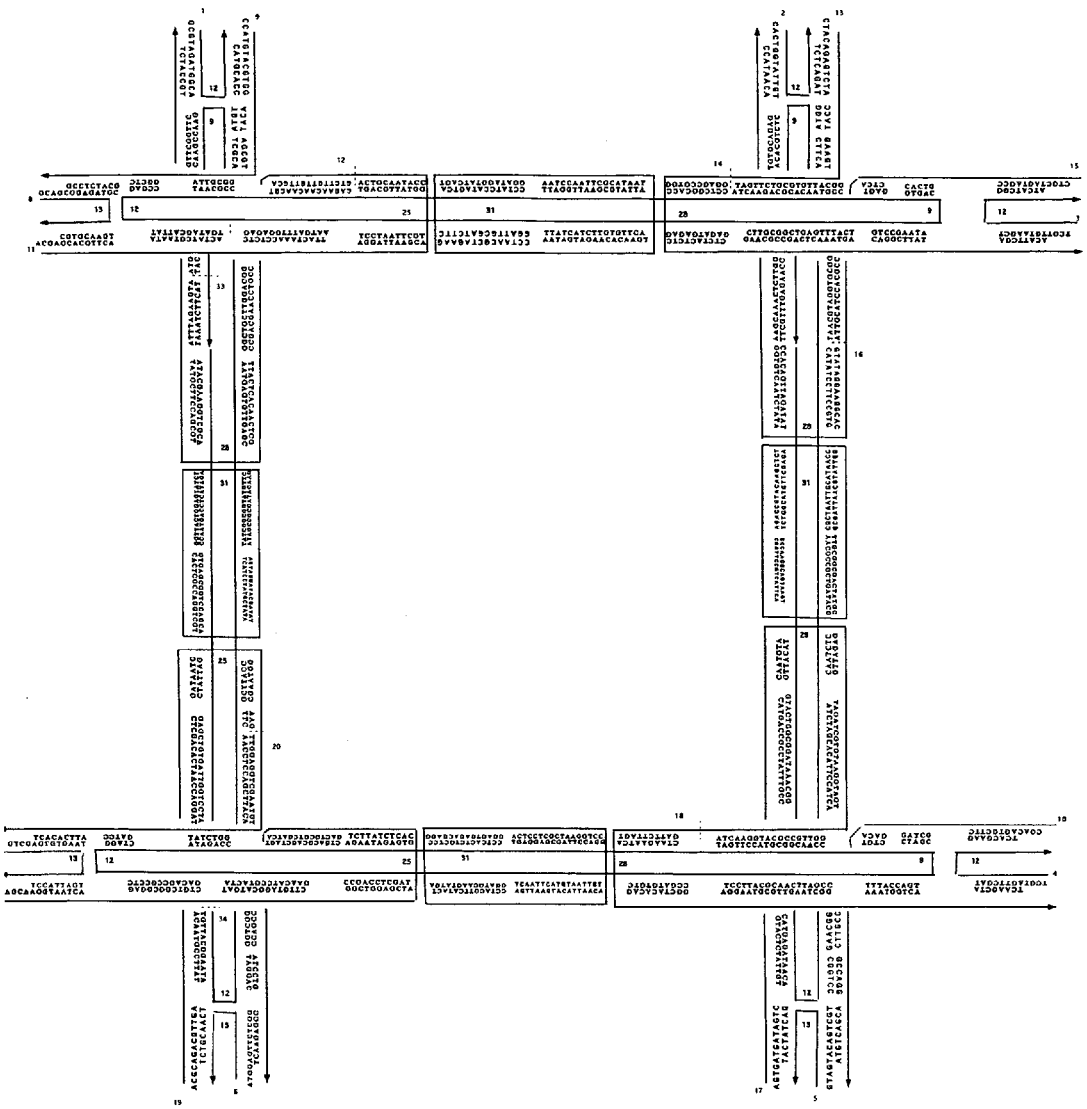
FIG. 17 schematically shows the arrangement shows the arrangement and nucleotide sequences (SEQ ID NOs:119 to 152) of a DX parallelogram (PDX-E-O) presented in FIG. 16.
Figure 18A:
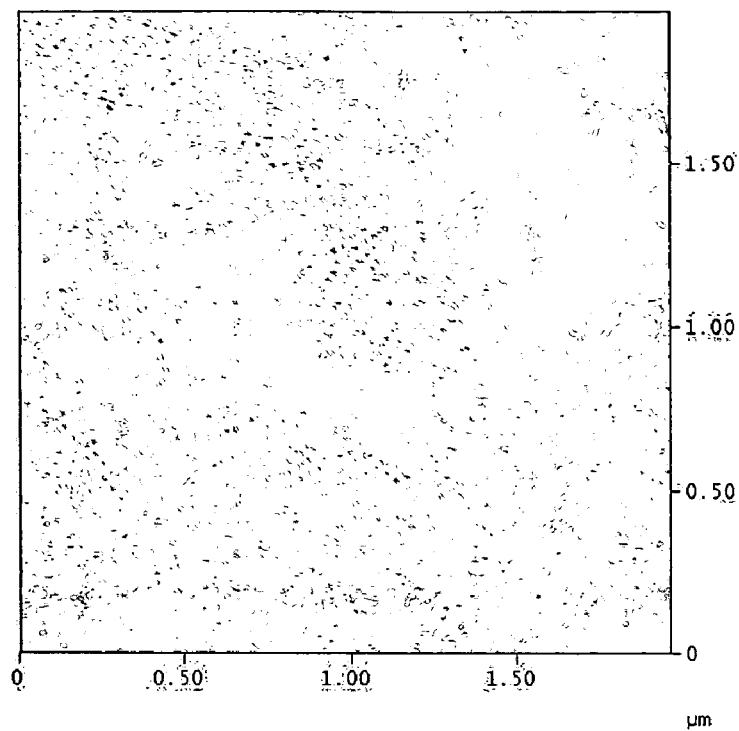
FIGS. 18A-18D are AFM images of the 2D lattice formed from the PDX-E-O parallelogram motif shown in FIGS. 16 and 17.
Figure 18B:
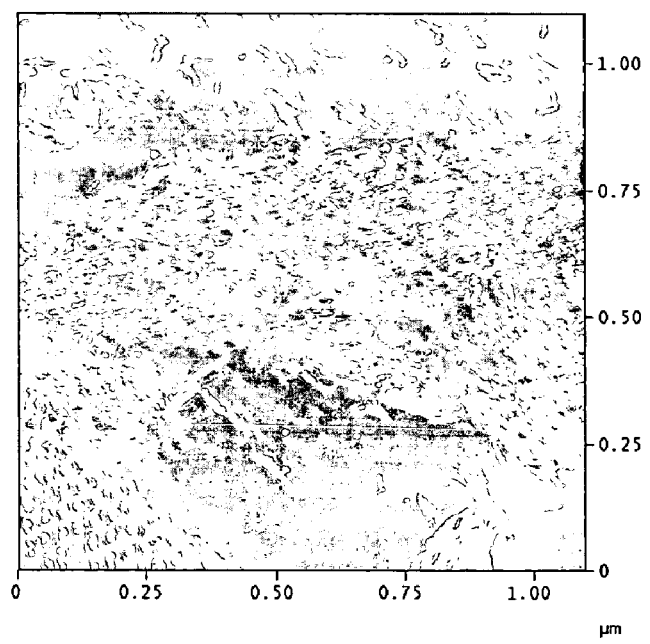
Figure 18C:
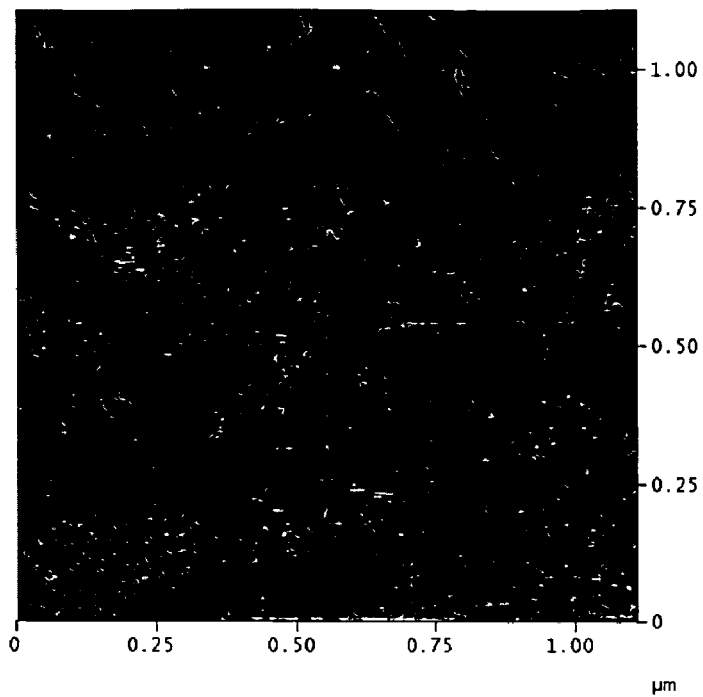
Figure 18D:
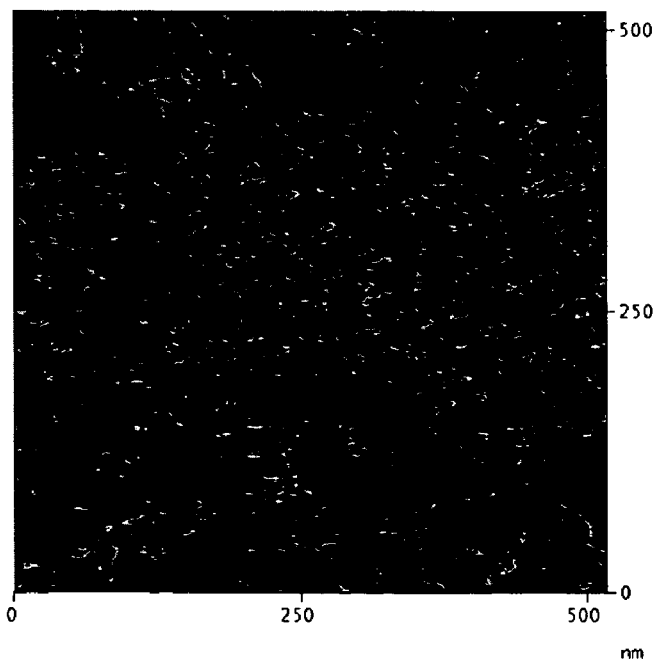

A 2D system based on DNA parallelograms (Mao et al., 1999) has also proved to be intractable when single helices (single sticky/cohesive ends) were used, but has led to visible arrays when DX molecules with double sticky/cohesive ends are used. The initial parallelogram system was based on systems where there was one helical turn beyond each crossover point, and four helical turns between them (Mao et al., 1999). Two versions of the DX parallelogram with double sticky/cohesive ends were designed. DX molecules are characterized by the relative orientations of their helices and the number of half helical turns between junction points. The orientations of the helices were antiparallel in both designs, but the number of half helical turns between junctions differed. The first version was designed to have all even number of half helical turns between junctions and therefore this molecule is called the PDX-E-E. The periodicity of this molecule was 40 nm. SEQ ID NOs: 65-96 were designed as the strand sequences of this PDX-E-E DNA parallelogram (FIG. 14). When the system was doubled to two helical turns beyond the vertices and eight helical turns between them, lattices were not obtained. This motif is shown in FIG. 13. It is clear from FIGS. 15A and 15B that it is possible to form parallelogram arrays from the motif in FIGS. 13 and 14, which was previously impossible. This design did not yield an extensive, well-ordered array, and the angle could not be accurately measured for this motif. The second version was designed to have a repeating pattern of every other number of half helical turns between junctions being even and odd and therefore this molecule is called the PDX-E-O (FIGS. 16 and 17). The overall periodicity of this molecule was also measured to be 41 nm and the torsion angles between the arms of branched junctions were measured to be 52°, as illustrated in the AFM images (FIG. 18A-18D). The arrays have small cavities of 14 nm and large cavities of 27 nm. These new designs provide a larger size parallelogram that has utility in patterning.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention.

Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Brun, Y., Gopalkrishnan, M., Reishus, D., Shaw, B., Chelyapov, N. and Adleman, L., Building Blocks for DNA Self-Assembly, In: *Foundations of Nanoscience: Self-Assembled Architectures and Devices*, ed. by J. Reif, a Symposium at Snowbird, Utah, April 21-23, pp. 2-15, Science Technica, Inc. (2004)

Caruthers, M. H., Gene synthesis machines:DNA chemistry and its uses, *Science*, 230:281-285 (1985)

Fu, T.-J.; Seeman, DNA Double Crossover Structures, *Biochemistry*, 32:3211-3220 (1993)

Kappraff, J., *Connections*, McGraw-Hill, New York, 209-253 (1990)

LaBean, T.; Yan, H.; Kopatsch, J.; Liu, F.; Winfree, E.; Reif, J. H.; Seeman, The Construction, Analysis, Ligation and Self-Assembly of DNA Triple Crossover Complexes, N. C. *J. Am. Chem. Soc.*, 122:1848-1860 (2000)

Li, X.; Zhan, Z.-Y. J.; Knipe, R.; Lynn, D. G., *J. Am. Chem. Soc.*, 124:746 (2002)

Liu, B.; Leontis, N. B.; Seeman, N. C. *Nanobiol.*, 3:177-188 (1994)

Liu, D.; Wang, M.; Deng, Z.; Walulu, R.; Mao, Tensegrity: Construction of Rigid DNA Triangles from Flexible Four-Arm DNA Junctions, C. *J. Am. Chem. Soc.*, 126:2324-2325 (2004)

Ma, R.-I.; Kallenbach, N. R.; Sheardy, R. D.; Petrillo, M. L.; Seeman, N. C., 3-Arm Nucleic Acid Junctions Are Flexible, *Nucl. Acids Res.*, 14:9745-9753 (1986)

Mao, C.; Sun, W.; Seeman, N. C., Designed Two-Dimensional DNA Holliday Junction Arrays Visualized by Atomic Force Microscopy, *J. Am. Chem. Soc.*, 121:5437-5443 (1999)

Mathieu, F.; Mao, C.; Seeman, N. C., A DNA Nanotube Based on a Six-helix Bundle Motif, *J. Biomol. Struct &Dyns.*, 18:907-908 (2001)

Piccirilli, J. A.; Krauch, T.; Moroney, S. E.; Brenner, S. A., *Nature*, 343:33-37 (1990)

Qi, J.; Li, X.; Yang, X.; Seeman, N. C., *J. Am. Chem. Soc.*, 118:6121-6130 (1996)

Rhodes, D.; Klug, A., Helical Periodicity of DNA Determined by Enzyme Digestion, *Nature* 286:573-578 (1980)

Sa-Ardyen, P.; Vologodskii, A. V.; Seeman, N. C., The Flexibility of DNA Double Crossover Molecules, *Biophys. J.* 84:3829-3837 (2003)

Seeman, N. C., DNA in a material world, *Nature*, 421:427-431 (2003)

Seeman, N. C., *J. Biomol. Str. &Dyns.* 8: 573-581 (1990)

Seeman, N. C., In: Biomolecular Stereodynamics, ed. R. H. Sarma, Academic Press, pp. 269-277 (1981)

Seeman, N. C., *J. Theor. Biol.* 99:237-247 (1982)

Wang, J. C., Helical Repeat of DNA in Solution, *Proc. Nat. Acad. Sci.* (*USA*) 76:200-203 (1979)

Winfree, E.; Liu, F.; Wenzler, L. A.; Seeman, N. C., Design and Self-Assembly of Two-Dimensional DNA Crystals, *Nature*, 394:539 (1998)

Yan. H.; Park, S. H.; Finklestein, G.; Reif, J. H.; LaBean, T. H., DNA-Templated Assembly of Protein Arrays and Highly Conductive Nanowires, *Science*, 301:1882-1884 (2003)

Yang, X., Wenzler, J. Qi, X. Li and N. C. Seeman, Ligation of DNA Triangles Containing Double Crossover Molecules, *Journal of the American Chemical Society* 120:9779-9786 (1998)

What is claimed is:

1. A polynucleic acid structure, comprising a polygonal unit whose edges are parallel helices of connected nucleic acid multi-crossover domains along their helix axes, each of said edges having at least one free end with two parallel helices, wherein each of said two parallel helices at one free end of each of said edges terminate in a cohesive end to provide a double cohesive end on said one free end.

2. The polynucleic acid structure of claim 1, wherein said nucleic acid multi-crossover domains are double crossover domains.

3. The polynucleic acid structure of claim 1, wherein said nucleic acid multi-crossover domains are triple crossover domains.

4. The polynucleic acid structure of claim 1, wherein said polygonal unit is a triangle.

5. The polynucleic acid structure of claim 1, wherein said polygonal unit is a parallelogram.

6. The polynucleic acid structure of claim 1, wherein each of said edges has a single free end with two parallel helices, and each of said two parallel helices at said single free end terminate in a cohesive end to provide a double cohesive end on each of said single free end.

7. The polynucleic acid structure of claim 1, wherein each of said edges has two free ends, each with two parallel helices, and each of said parallel helices of said free ends terminate in a cohesive end to provide double cohesive ends on said free ends.

8. The polynucleic acid structure of claim 1, wherein the cohesive ends on said two parallel helices are different.

9. The polynucleic acid structure of claim 1, wherein:
said polygonal unit is a triangle having as edges connected nucleic acid double crossover domains;
each of said edges has a single free end with two parallel helices; and
each of said two parallel helices at said single free end terminate in a cohesive end to provide a double cohesive end on said single free end.

10. The polynucleic acid structure of claim 1, wherein:
said polygonal unit is a triangle having as edges connected nucleic acid triple crossover domains;
each of said edges has two free ends each with two parallel helices; and
each of said two parallel helices terminate in a cohesive end to provide double cohesive ends on each of said free ends.

11. The polynucleic acid structure of claim 1, wherein:
said polygonal unit is a parallelogram having as edges nucleic acid double crossover domains;
each of said edges has two free ends each with two parallel helices; and
each of said two parallel helices terminate in a cohesive end to provide double cohesive ends on each of said free ends.

12. The polynucleic acid structure of claim 1, which is an array of polygonal units linked together by complementary double cohesive ends.

13. The polynucleic acid structure of claim 12, wherein said array is an array of triangular units linked together by complementary double cohesive ends to form a trigonal lattice.

14. The polynucleic acid structure of claim 12, which is an array of two different triangular units linked together by complementary double cohesive ends to form a trigonal lattice.

15. The polynucleic acid structure of claim 12, wherein said array is an array of parallelogram units linked together by complementary double cohesive ends.

16. A method for producing the polynucleic acid structure of claim 1, comprising:
synthesizing single stranded polynucleotides, each being designed to be self-complementary and/or complementary to another single stranded polynucleotide so as to be capable of self-annealing into a polygonal unit;
mixing the single stranded polynucleotides to form a mixture of polynucleotides and heat denaturing the mixture; and
annealing the heat denatured mixture of single stranded polynucleotides to form the polygonal unit by self-assembly.

17. The method of claim 16, further comprising:
heating the annealed polygonal unit to ensure exposed cohesive ends; and
annealing exposed complementary cohesive ends of a plurality of the annealed polygonal unit to form an array of polygonal units.

18. The method of claim 16, wherein two different polygonal units are separately formed and wherein the method further comprises:
heating the two different annealed polygonal units to ensure exposed cohesive ends; and
annealing the exposed cohesive ends that are complementary to form an array of two different polygonal units.

* * * * *